United States Patent
Tokumaru et al.

(10) Patent No.: US 9,932,555 B2
(45) Date of Patent: Apr. 3, 2018

(54) INCUBATOR CONVEYING SYSTEM, INCUBATOR DEPOSITORY AND ISOLATOR SYSTEM

(71) Applicant: PANASONIC HEALTHCARE HOLDINGS CO., LTD., Tokyo (JP)

(72) Inventors: Tomoyoshi Tokumaru, Gunma (JP); Akira Higuchi, Osaka (JP)

(73) Assignee: PANASONIC HEALTHCARE HOLDINGS CO., LTD., Tokyo (JP)

(*) Notice: Subject to any disclaimer, the term of this patent is extended or adjusted under 35 U.S.C. 154(b) by 54 days.

(21) Appl. No.: 15/044,718

(22) Filed: Feb. 16, 2016

(65) Prior Publication Data
US 2016/0160168 A1 Jun. 9, 2016

Related U.S. Application Data

(63) Continuation of application No. PCT/JP2014/081555, filed on Nov. 28, 2014.

(30) Foreign Application Priority Data

Dec. 4, 2013 (JP) ................................. 2013-250763
Dec. 4, 2013 (JP) ................................. 2013-250765
(Continued)

(51) Int. Cl.
*C12M 1/00* (2006.01)
*C12M 3/00* (2006.01)
(Continued)

(52) U.S. Cl.
CPC ............ *C12M 41/14* (2013.01); *C12M 23/44* (2013.01); *C12M 29/00* (2013.01); *C12M 29/20* (2013.01); *C12M 37/00* (2013.01); *B01L 1/025* (2013.01)

(58) Field of Classification Search
CPC ...... C12M 23/40; C12M 23/48; C12M 23/50; C12M 41/12; C12M 41/14
See application file for complete search history.

(56) References Cited

U.S. PATENT DOCUMENTS 6,673,595 B2 * 1/2004 Barbera-Guillem ... C12M 23/24
435/286.2
2002/0090320 A1 * 7/2002 Burow .................... B01L 9/523
422/64

(Continued)

FOREIGN PATENT DOCUMENTS

JP 2006-115798 A 5/2006
JP 2006-149232 A 6/2006
(Continued)

OTHER PUBLICATIONS

Extended European Search Report issued in European Application No. 14867701.6 dated Aug. 8, 2016.
(Continued)

*Primary Examiner* — Nathan A Bowers
(74) *Attorney, Agent, or Firm* — McDermott Will & Emery LLP

(57) ABSTRACT

The present invention includes a conveyor body which partitions a plurality of storage chambers, a connection opening connected to an external device, and a conveying chamber that connects the plurality of storage chambers to the connection opening, a plurality of incubators detachably stored in the plurality of incubators, a conveyor device that conveys one of the plurality of incubators from the storage chamber to the connection opening, and an environment control device that individually controls an interior environment of the plurality of incubators by supplying and discharging gas to and from each incubator.

20 Claims, 22 Drawing Sheets

(30) Foreign Application Priority Data

| Dec. 4, 2013 | (JP) | ................................ 2013-250766 |
| Dec. 4, 2013 | (JP) | ................................ 2013-250768 |
| Dec. 4, 2013 | (JP) | ................................ 2013-250769 |

(51) Int. Cl.
*C12M 1/12* (2006.01)
*B01L 1/02* (2006.01)

(56) References Cited

U.S. PATENT DOCUMENTS

| 2004/0147012 A1* | 7/2004 | Yokoi ................... C12M 23/48 435/303.1 |
| 2005/0130297 A1* | 6/2005 | Sarem ................... C12M 23/12 435/297.1 |
| 2006/0151185 A1* | 7/2006 | Takagi ..................... A61L 2/07 172/4 |
| 2008/0113426 A1* | 5/2008 | Smith ..................... C12M 23/34 435/286.5 |
| 2009/0141345 A1* | 6/2009 | Tsuchiya ................ B01L 9/523 359/393 |
| 2011/0070631 A1 | 3/2011 | Kiyota |
| 2011/0189765 A1 | 8/2011 | Fukui et al. |
| 2012/0273047 A1 | 11/2012 | Yokoi et al. |
| 2013/0273646 A1 | 10/2013 | Kobayashi et al. |

FOREIGN PATENT DOCUMENTS

| JP | 2012-231726 A | 11/2012 |
| JP | 2013-135858 A | 7/2013 |
| WO | 93/24234 A2 | 12/1993 |
| WO | 2013/047290 A1 | 4/2013 |

OTHER PUBLICATIONS

International Search Report issued in Application No. PCT/JP2014/081555 dated Feb. 24, 2015, with English translation.

* cited by examiner

| | STORAGE CHAMBER 21 | STORAGE CHAMBER 22 | STORAGE CHAMBER 23 | STORAGE CHAMBER 24 | STORAGE CHAMBER 25 | STORAGE CHAMBER 26 |
|---|---|---|---|---|---|---|
| CONVEYOR BODY | --- | IDENTIFICATION INFORMATION A | IDENTIFICATION INFORMATION B | IDENTIFICATION INFORMATION C | --- | --- |

| | DEPOSITORY CHAMBER 41 | DEPOSITORY CHAMBER 42 | DEPOSITORY CHAMBER 43 | DEPOSITORY CHAMBER 44 | DEPOSITORY CHAMBER 45 | DEPOSITORY CHAMBER 46 |
|---|---|---|---|---|---|---|
| DEPOSITORY BODY | IDENTIFICATION INFORMATION D | --- | IDENTIFICATION INFORMATION E | --- | IDENTIFICATION INFORMATION F | IDENTIFICATION INFORMATION G |

FIG. 14

INCUBATOR CONVEYING SYSTEM, INCUBATOR DEPOSITORY AND ISOLATOR SYSTEM

CROSS-REFERENCE TO RELATED APPLICATIONS

This is a continuation application of International Patent Application No. PCT/JP2014/081555 filed Nov. 28, 2014, which claims the benefit of priority to Japanese Patent Application No. 2013-250763, Japanese Patent Application No. 2013-250765, Japanese Patent Application No. 2013-250766, Japanese Patent Application No. 2013-250768, and Japanese Patent Application No. 2013-250769, filed Dec. 4, 2013. The full contents of the International Patent Application are incorporated herein by reference.

BACKGROUND

Technical Field

The present disclosure relates to an incubator conveying system, an incubator depository and an isolator system.

There is known, for example, an isolator having a working chamber in which culture work and the like of a body to be cultured are performed (Japanese Patent Application Laid-open Publication No. 2013-135858). For example, in a case where work for performing culture and the like of a body to be cultured takes place using the isolator the above publication, there is a need to connect the incubator to the isolator in order to move to the work chamber the body to be cultured from the incubator where the body to be cultured is stored. This connection of the incubator to the isolator has to be performed by a person and there may be a problem that the work for moving the body to be cultured from the incubator to the work chamber may be troublesome.

SUMMARY

The principal invention of the present application for solving the above problem is an incubator conveying system including a conveyor body configured to have partitioned a plurality of storage chambers, a first opening connected to an external device, a conveying chamber that connects the plurality of storage chambers and the first opening, a plurality of incubators demountably stored in the plurality of chambers, a conveyor device configured to convey one of the plurality of the incubators from the storage chamber to the first opening; and an environment control device configured to supply and discharges gas to and from each of the incubators and control each interior environment of the plurality of the incubators.

Other features of the present invention will become apparent from descriptions of the present specification and of the accompanying drawings.

BRIEF DESCRIPTION OF THE DRAWINGS

For more thorough understanding of the present invention and advantages thereof, the following description should be read in conjunction with the accompanying drawings, in which:

FIG. 14 is a diagram illustrating incubator information according to the first embodiment of the present invention;

DETAILED DESCRIPTION

At least the following details will become apparent from description of this specification and of the accompanying drawings.

First Embodiment

Isolator System

Figure 1:
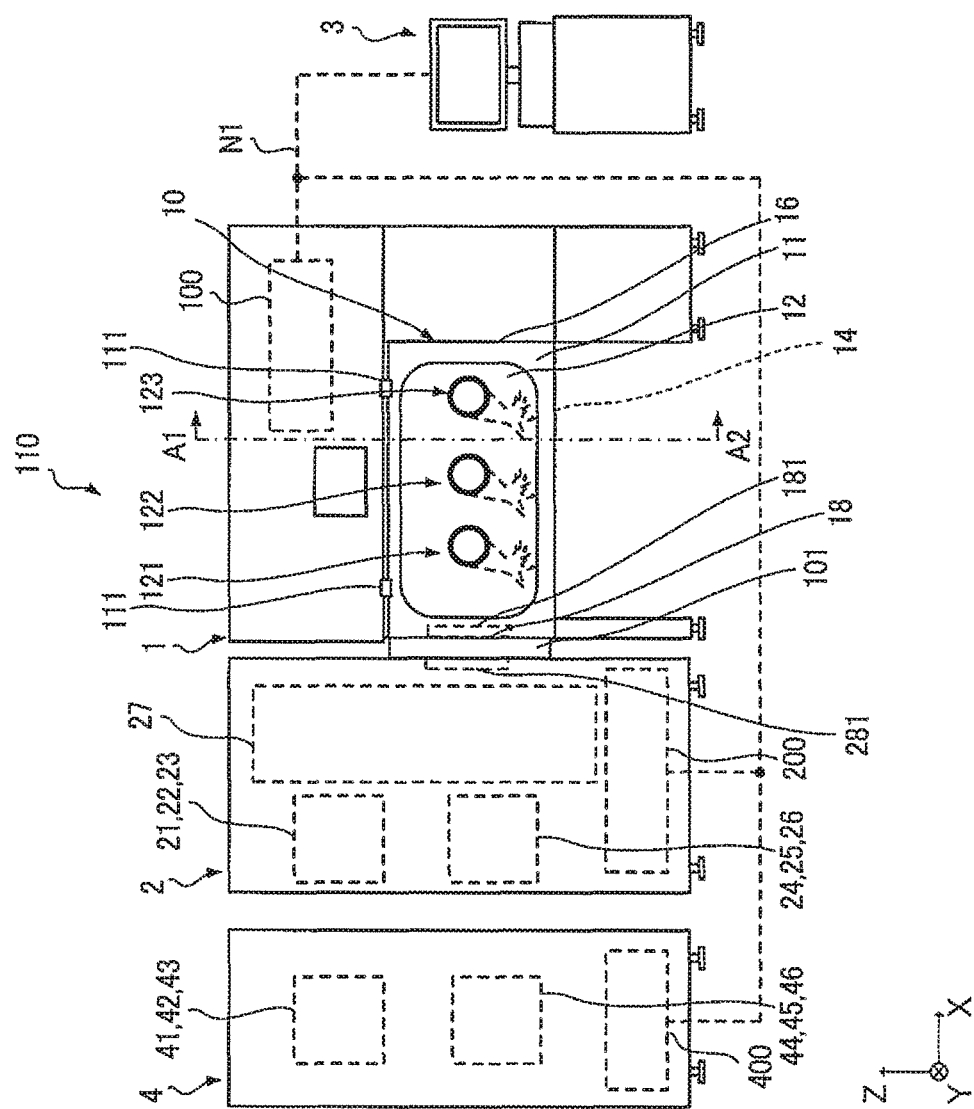
FIG. 1 is a front view illustrating an isolator system according to a first embodiment of the present invention.

An isolator system according to an embodiment of the present invention will be described hereinafter with reference to FIG. 1. FIG. 1 is a front view illustrating an isolator system according to the present embodiment. Here, the Z axis is an axis which comes along the vertical direction in which the isolator system 110 is vertically arranged with the direction extending from the lower side toward the upper side being referred to as the +Z direction and the direction extending from the upper side toward the lower side being referred to as the −Z direction. The X axis is an axis that comes along the direction in which the conveyor body 2 and the isolator 1 come adjacent to each other with the direction extending from the conveyor body 2 toward the isolator 1 being referred to as the +X direction and the direction extending from the isolator 1 toward the conveyor body 2 being referred to as the −X direction. The Y axis is an axis which is orthogonal to the X axis as well as the Z axis with the direction extending from the door 11 of the isolator 1 toward the back plate 14 which is on the opposite side of the door 11, along the Y axis, being referred to as the +Y direction and the direction extending from the back plate 14 toward the door 11 being referred to as the −Y direction.

The isolator system 110 refers to a system including an isolator 1 (external device), a conveyor body 2, a depository body 4, a control device 3 and an incubator 5 (FIG. 8), and is provided in, for example, a laboratory. Further, the incubator conveying system refers to a system including a conveyor body 2, and an incubator 5, a conveyor device 9 and the like which are provided inside the conveyor body 2, and this system is connected to an external device of, for example, the isolator 1 and the like. The incubator conveying system configures a part of the isolator system 110 by being connected to, for example, the isolator 1.

The isolator 1 is a device used to perform, for example, work for culturing, manipulating, observing and the like a body to be cultured (culture) of cells and the like, in a sterilized environment. Here, sterilization means an act of killing microorganisms, cells and the like, to bring a state closer to a sterile environment by supplying sterilizing gas.

The conveyor body 2 is a device which conveys to the isolator 1 side a predetermined incubator among the incubators 5 (FIG. 8) stored inside a plurality of storage chambers 21 to 26, and is coupled (connected) to the isolator 1 via the coupling unit 101. Here, the conveyor body 2 is detachable from the isolator 1 and may be allowed to couple with another isolator having a configuration similar to that of the isolator 1.

The depository body 4 is a device to deposit the incubators in the plurality of the depository chambers 41 to 46. The depository body 4 is provided in the periphery of the conveyor body 2 to allow easy work for storing the incubators 5 taken out from the depository chambers 41 to 46 into the storage chambers 21 to 26 of the conveyor body 2, and storing the incubators 5 taken out from the storage chambers 21 to 26 into the depository chambers 41 to 46.

The control device 3 is connected to the respective control devices 100, 200 and 400 of the isolator 1, the conveyor body 2 and the depository body 4 (also referred to as "the devices") to control the devices. Here, the function of the control device 3 may be included in any one of the devices. Additionally, each of the devices may include an input device to allow individual control by inputting information to the respective input device.

The incubator 5 is a cassette type incubator used to culture the body to be cultured.

===Isolator===

Figure 2:
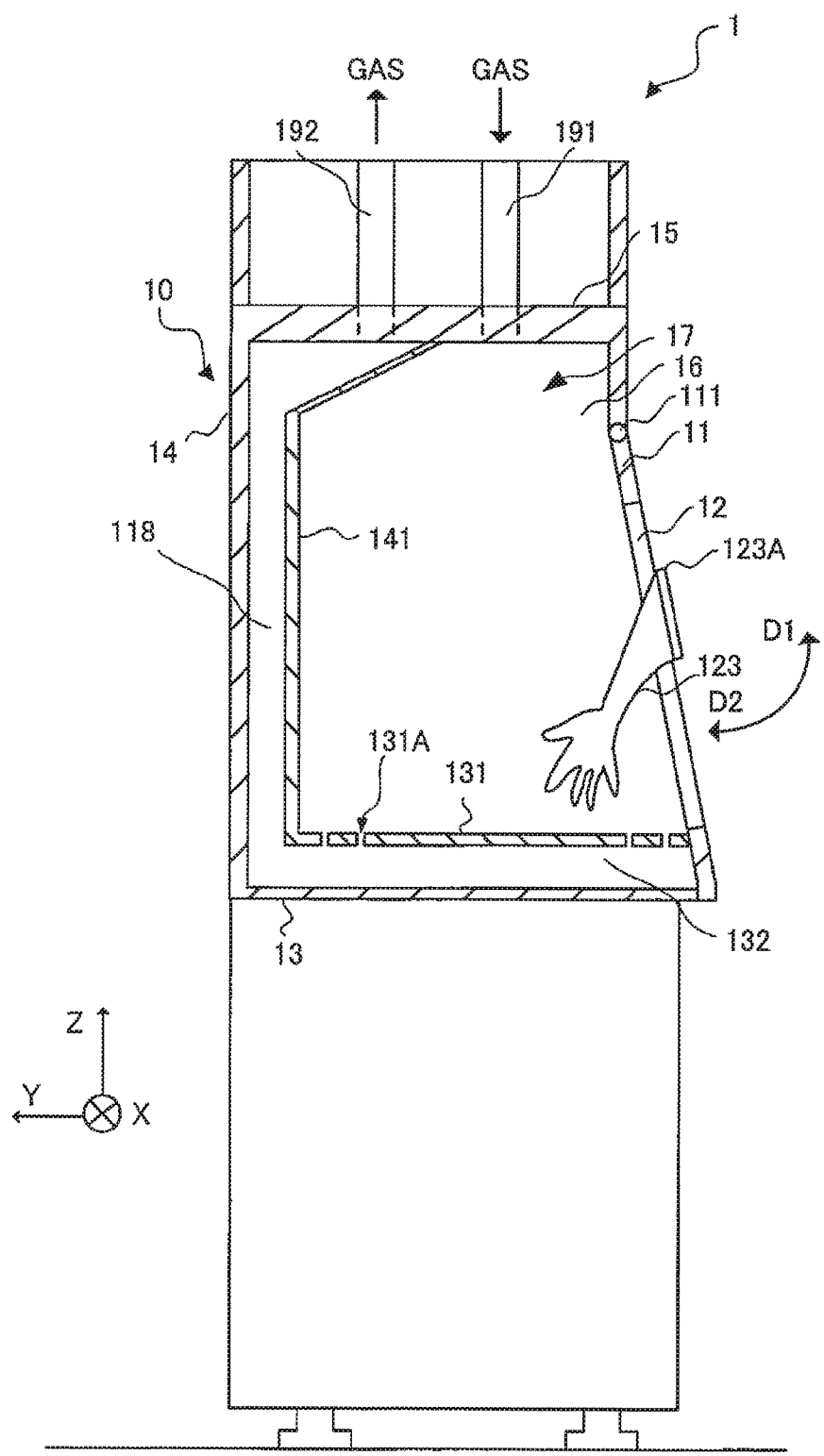
FIG. 2 is a sectional view illustrating the isolator according to the first embodiment of the present invention.

The isolator according to the present embodiment will be described in the following with reference to FIGS. 1 and 2. FIG. 2 is a sectional view illustrating the isolator according to the present embodiment. FIG. 2 is a sectional view seen toward the +X side from the section cut along line A1-A2 in FIG. 1.

Figure 11:
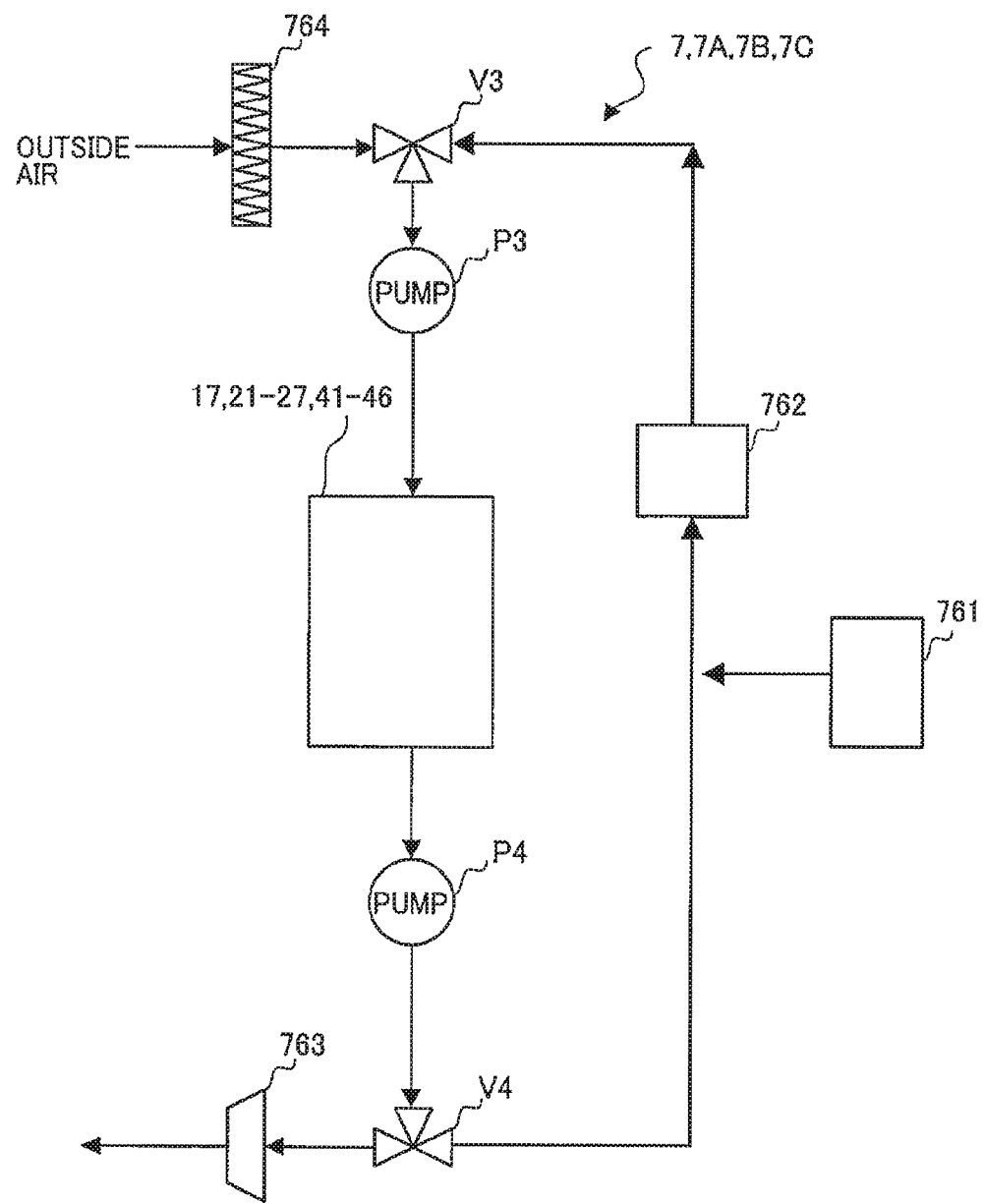
FIG. 11 is a view illustrating a first gas circulation circuit according to the first embodiment of the present invention.

The isolator 1 includes a chamber 10 and a first gas circulation circuit 7A (FIG. 11).

The chamber 10 is a metal box in a substantially rectangular parallelepiped form and includes therein a working chamber 17. The chamber 10 has the interior and the exterior thereof separated by the door 11, bottom plate 13, the back plate 14, the top plate 15, the side plate 18 (FIG. 1) and the side plate 16 (also referred to as the "shell member of the chamber 10".) Here, the shell member of the chamber 10 may be formed by bending and welding or attaching, for example, predetermined metal plates so to restrain bacterial invasion from the exterior into the interior of the chamber 10 and also to keep the interior of the chamber 10 airtight.

The door 11 is provided to the front face (−Y) of the chamber 10. The door 11 is provided to rotate in the D1 direction or the D2 direction about a rotating shaft extending along the X axis and running through the hinge 111 provided to the upper part (+Z) of the door 11. Here, it is assumed that a sealing member such as a rubber gasket is provided to the edge of the door 11 to keep the interior of the chamber 10 airtight when the door 11 is rotated in the D2 direction and closed.

The door 11 has provided a transparent plate 12 made of, for example, resin and the like so that the interior of the chamber 10 can be seen from the outside of the chamber 10.

The transparent plate 12 is provided with, for example, three gloves 121, 122 and 123 which extend into the working chamber 17. The gloves 121, 122 and 123 are used when a worker outside the working chamber 17 performs work such as culture of the body to be cultured in the working chamber 17. The gloves 121, 122 and 123 are respectively mounted to the frames 121A, 122A and 123A so that a worker can perform work while the working chamber 17 is kept airtight.

The chamber 10 further includes a separation plate 141 and a work plate 131.

The work plate 131 exhibits a function as a work platform on which there are placed dishes, flasks and the like which contain the body to be cultured. The work plate 131 is a metal plate in a substantially rectangular shape when seen along the direction from +Z toward −Z and has provided a plurality of air holes 131A. The work plate 131 is provided above the bottom plate 13 so that a duct 132 for communicating gas between the work plate 131 and the bottom plate 13 can be equipped. Here, the gas can include air, sterilizing gas and the like which flow inside from the exterior of the isolator 1.

The separation plate 141 is a metal flat plate for separating from the working chamber 17 the duct 118 which communicates gas. The lower side end (−Z) of the separation plate 141 is coupled to the +Y side end of the work plate 131. The upper end (+Z) of the separation plate 141 is provided between the duct 191 and the duct 192.

The gas that has flown into the working chamber 17 through the duct 191 flows through the air communication holes 131A and the ducts 132, 118 and 192 and out of the chamber 10. The flowing in and out of the gas is controlled by the first gas circulation circuit 7A. Description of the first gas circulation circuit 7A will be given later.

===Conveyor Body===

Figure 3:
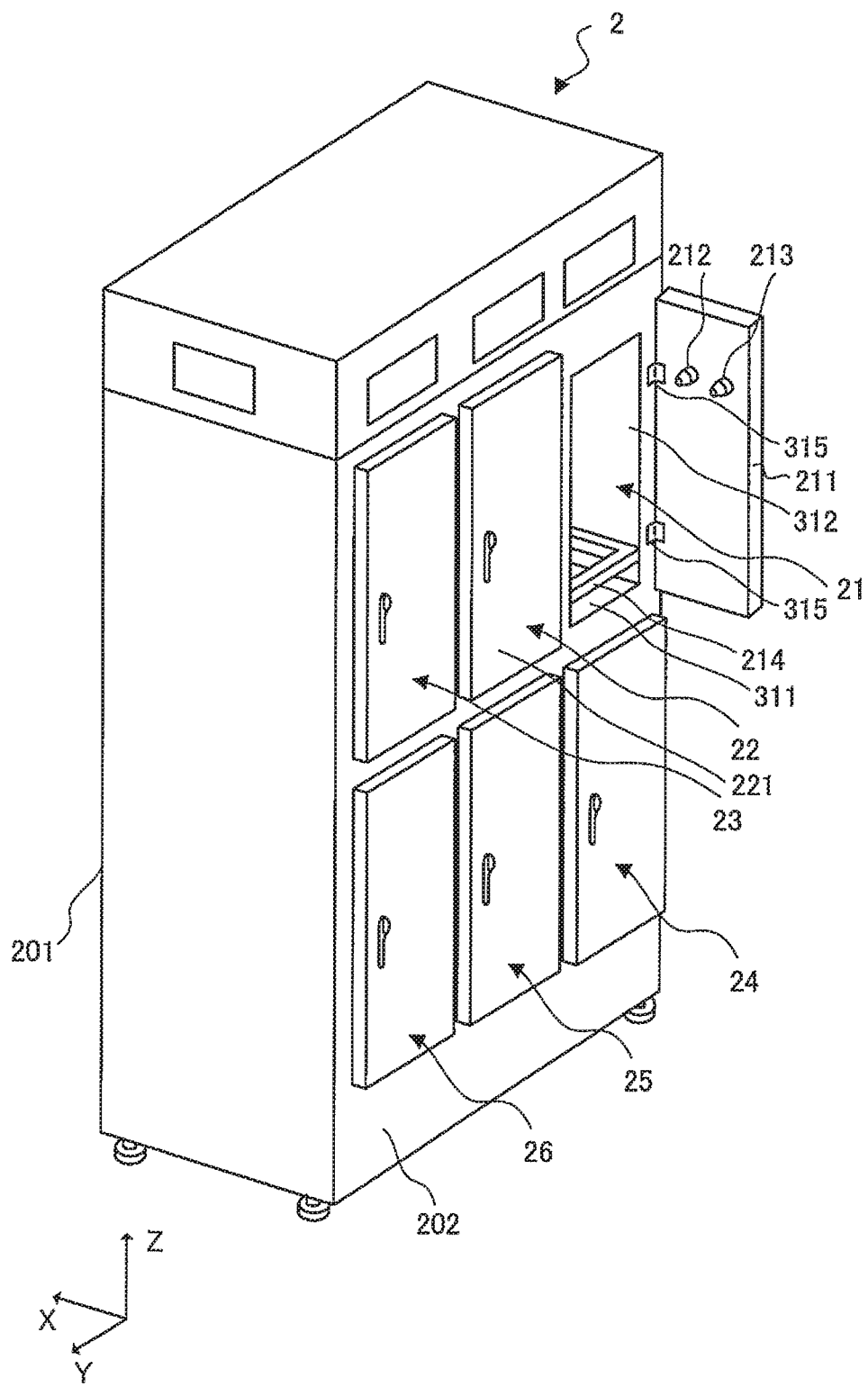
FIG. 3 is a perspective view illustrating the conveyor body according to the first embodiment of the present invention.
Figure 4:
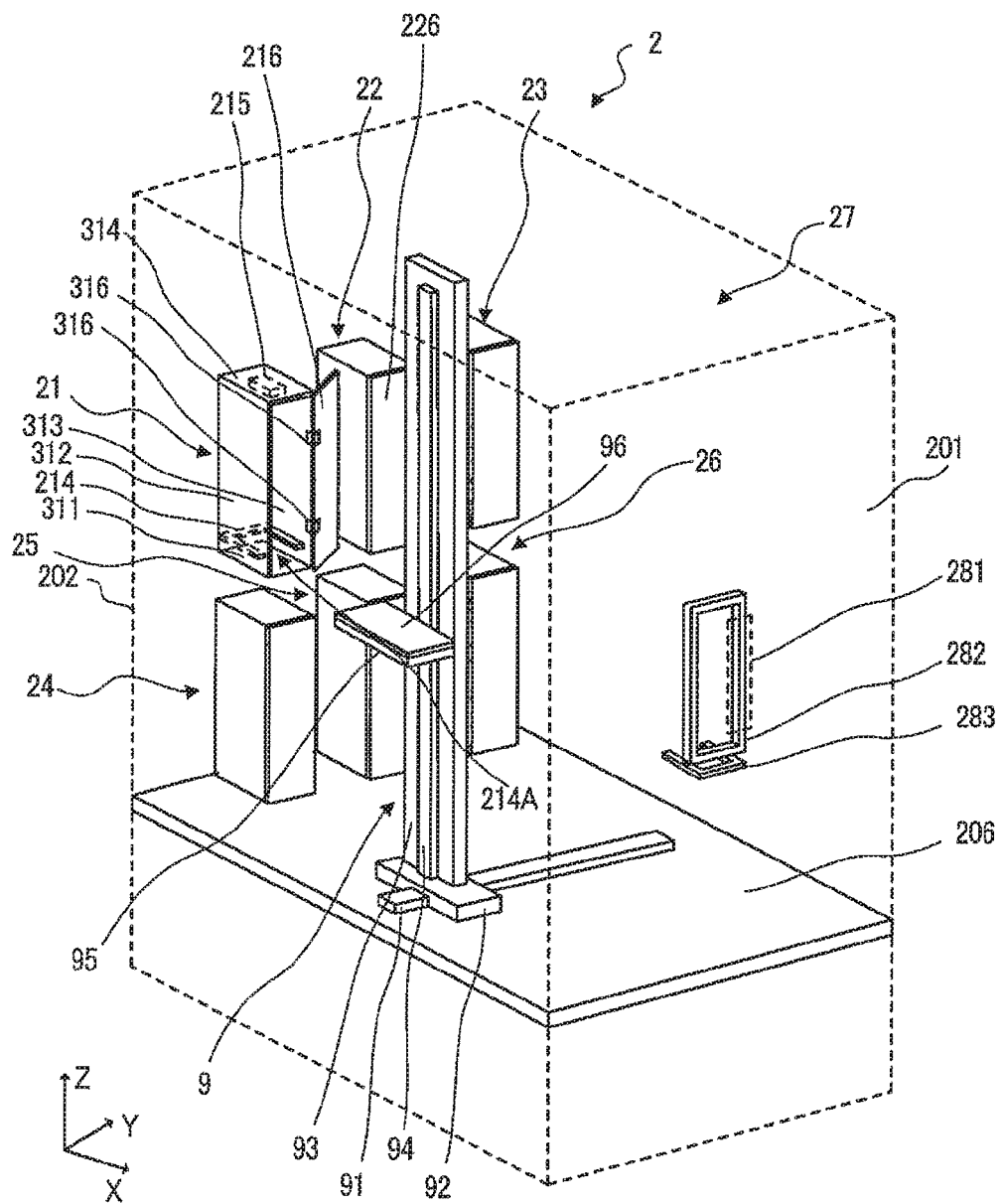
FIG. 4 is a transparent view illustrating the conveyor body according to the first embodiment of the present invention.
Figure 5:
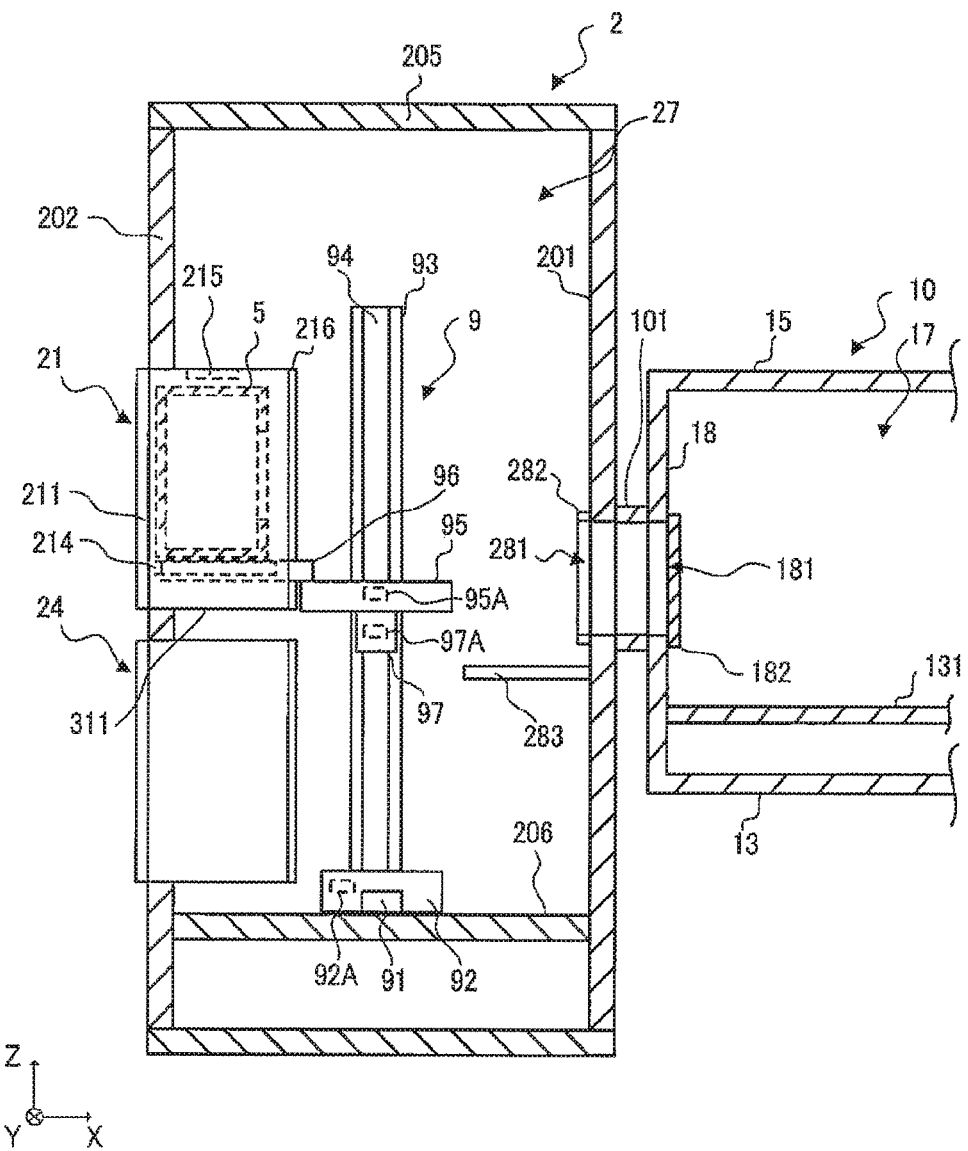
FIG. 5 is a sectional view illustrating the conveyor body and a chamber according to the first embodiment of the present invention.
Figure 6:
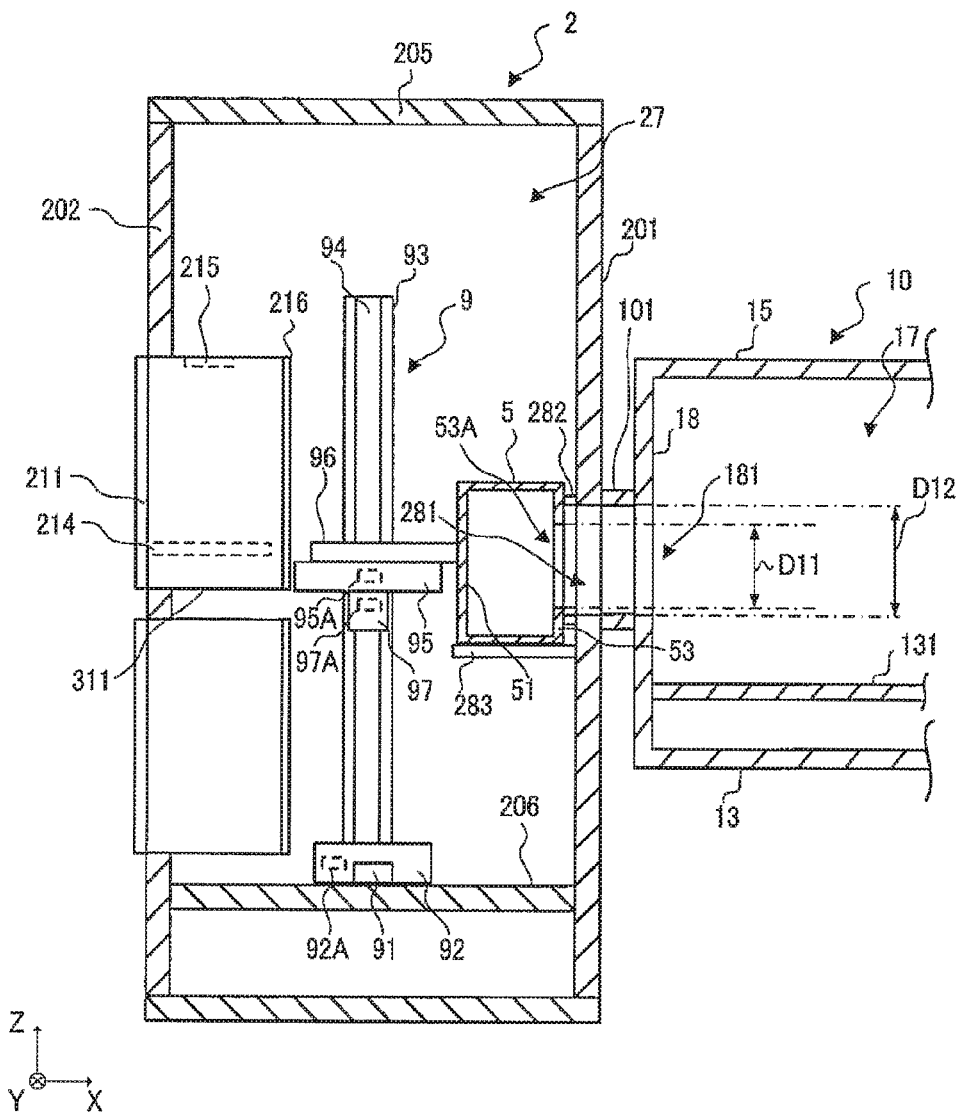
FIG. 6 is a sectional view illustrating the conveyor body and the chamber in a state having an incubator conveyed to a connection opening side according to the first embodiment of the present invention.

Description of the conveyor body according to the present embodiment will be given in the following with reference to FIGS. 1 and 3 through 6. FIG. 3 is a perspective view illustrating the conveyor body according to the present embodiment. FIG. 4 is a transparent view illustrating the conveyor body according to the present embodiment. In FIG. 4, the contour of the conveyor body 2 is indicated with broken lines and the parts inside the conveyor body 2 are indicated with solid lines. Although a part of the mounting table 214 and the reading device 215 cannot be seen, they are indicated in broken lines for the purpose of illustration. FIG. 5 is a sectional view illustrating the conveyor body and the chamber according to the present embodiment. FIG. 6 is a sectional view illustrating the conveyor body and the chamber in a state having the incubator conveyed to the connection opening side according to the present embodiment. FIGS. 5 and 6 illustrate the conveyor body 2 and the isolator 1 when seen toward the +Y direction from a section parallel to the XZ plane on the −Y side with respect to the storage chamber 21 in FIG. 4. The incubator 5 in FIGS. 5 and 6 are illustrated as sectional views seen toward the +Y direction from a section which runs through the center of the incubator 5 as well as is parallel to the XZ plane for the purpose of illustration. Meanwhile, FIG. 5 has the chamber 10 illustrated with the door 182 in a closed state. Although FIG. 6 illustrates the door 182 in an open state, the door 182 is omitted for the purpose of illustration.

The conveyor body 2 is a device used to perform sterilizing and conveying the incubator 5 inside the conveyor body 2. The conveyor body 2 is provided with the back plate 201 opposing the side plate 18 of the isolator 1.

The conveyor body 2 is a metal box in a substantially rectangular parallelepiped form. The contour of the conveyor body 2 including the front plate 202 and the back plate 201 may be formed by, for example, bending and welding or attaching predetermined metal plates so to restrain bacterial invasion from the exterior to the interior of the conveyor body 2 and also to keep the interior of the conveyor body 2 airtight.

The conveyor body 2 includes the storage chambers 21 to 26, the conveying chamber 27, the conveyor device 9, the first gas circulation circuit 7A and the second gas circulation circuit 6. In other words, the conveyor body 2 has partitioned at least the storage chambers 21 to 26, the conveying chamber 27 and the later described connection opening 281 as the first opening.

=Storage Chamber=

The storage chambers 21 to 26 are vertically arranged side by side in pairs so that there are three storage chambers arranged along the horizontal direction (Y axis). Here, the number of storage chambers provided to the conveyor body 2 may be less than six or more than six. And the storage chambers need not be arranged side by side along the vertical direction and the horizontal direction.

The interiors of the storage chambers 21 to 26 are separated from each other and further separated from the conveying chamber 27. The structures of the storage chambers 21 to 26 are the same with each other so that description of only the storage chamber 21 will be given and description of the structures of the storage chambers 22 to 26 will be omitted.

The storage chamber 21 is structured with the doors 211 and 216, the bottom plate 311, the side plates 312 and 313 and the top plate 314 so that the shape of the interior is in a substantially rectangular parallelepiped form. The inner shape of the storage chambers 21 is formed to be larger than the contour of the incubator so that the incubator 5 can be stored inside the storage chamber 21. The interior of the storage chamber 21 may be chamfered to allow easy cleaning.

The door 211 is in a substantially rectangular parallelepiped form and is used to open/close the storage chamber 21. The door 211 is provided on the −X side of the storage chamber 21 and separates the interior of the storage chamber 21 from the exterior thereof. The door 211 is provided to rotate about a rotating shaft extending along the Z axis running through the hinge 315. Here, a sealing member such as a rubber gasket may be provided to the edge of the door 211 to keep the interior of the storage chamber 21 airtight when the door 211 is closed.

The inner face of the door 211 facing the interior of the storage chamber 21 is equipped with a supply port 212 and a discharge port 213. The supply port 212 is used to supply gas to the interior of the incubator 5 which is stored in the storage chamber 21 and the discharge port 213 is used to discharge gas discharged from the incubator 5. In other words, gas flows out through the supply port 212 and gas flows in through the discharge port 213. The supply port 212 and the discharge port 213 are respectively provided at positions opposing the supply port 552 and the discharge port 553 of the incubator 5.

The first locking device equipped to the conveyor body 2 is locked when the door 211 is closed. In this way the door 211 cannot be opened. The first locking device is controlled by the control device 3 and performs the locking and the releasing of the door 211. When the first locking device releases the lock, the door 211 is openable.

Figure 10:
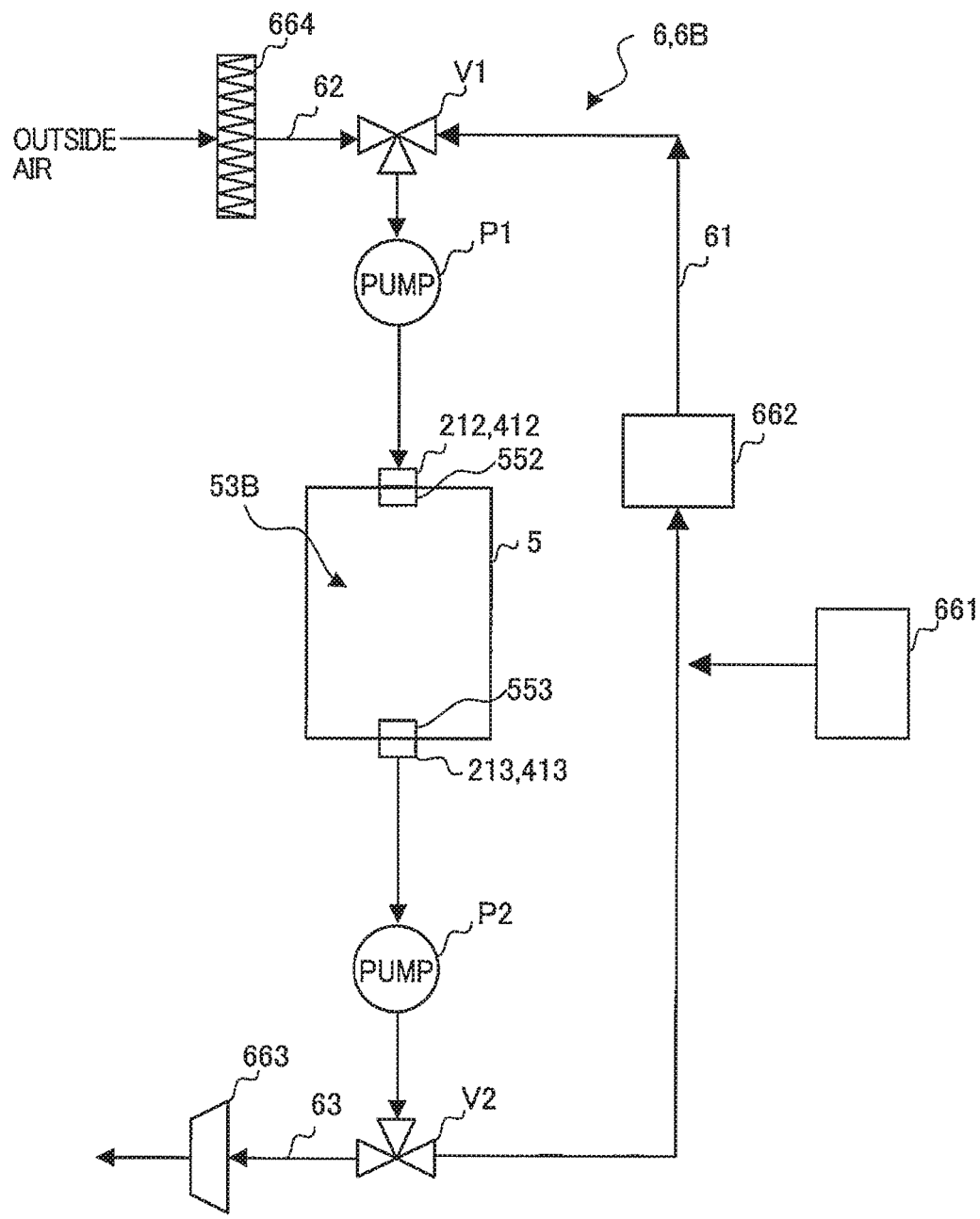
FIG. 10 is a view illustrating a second gas circulation circuit according to the first embodiment of the present invention.

When the door 211 is closed in a state having the incubator 5 stored in the storage chamber 21, the supply port 212 and the discharge port 213 are respectively connected to the supply port 552 and the discharge port 553 of the incubator 5. On the other hand, when the door 211 is opened, the supply port 212 and the discharge port 213 are released from the supply port 552 and the discharge port 553 of the incubator 5. The supply and the discharge of gas through the supply port 212 and the discharge port 213 are performed by the second gas circulation circuit 6 (FIG. 10). The details of the second gas circulation circuit 6 will be given later.

The door 216 is used to open/close the storage chamber 21 inside the conveying chamber 27. The door 216 is provided on the +X side of the storage chamber 21 and separates the interior of the storage chamber 21 from the exterior thereof. The door 216 is provided to rotate about a rotating shaft extending along the Z axis running through the hinge 316. The door 216 is automatically rotated by a motor (not shown) provided proximate the door 216. This motor is controlled by the control device 3. In other words, the opening/closing of the door 216 is controlled by the control device 3. Here, a sealing member such as a rubber gasket may be provided to the edge of the door 216 to keep the interior of the storage chamber 21 airtight when the door 216 is closed.

The storage chamber 21 has a reading device 215 and a mounting table 214 provided therein.

The reading device 215 is a device for reading out information stored in the tag 551 (FIG. 8) attached to the incubator 5. The reading device 215 is provided to a location of the top plate 314 which opposes the tag 551 of the incubator 5. Details of the reading device 215 will be given later.

The incubator 5 is mounted on the mounting table 214. The mounting table 214 is in a substantially laterally facing U-form when seen in the direction from the +Z side toward the −Z side. The mounting table 214 is arranged above (+Z side) the bottom plate 311 to provide a space for inserting the conveying table 96 (FIG. 4) in this space formed, in the Z axis direction, between the mounting table 214 and the bottom plate 311. The mounting table 214 includes a notch part 214A that is cut off, from the mounting table 214, from the +X direction toward the −X direction. The width of the notch part 214A along the Y axis direction is set longer than the width of the conveying table 96 along the Y axis direction and shorter than the width of the incubator 5 along the Y axis direction avoiding contact with the conveying table 96.

Additionally, the storage chamber 21 has provided an inlet hole (not shown) for gas to flow into the storage chamber 21 and an outlet hole (not shown) for gas to flow out of the storage chamber 21 and the first gas circulation circuit 7 allows the gas to flow in and out. Description of the first gas circulation circuit 7 will be given later.

The temperature, the humidity, the carbon dioxide concentration and the like in the storage chamber 21 is controlled using the gas in the first gas circulation circuit 7, and condensation inside the incubator 5 is prevented by heating the storage chamber 21 and not allowing cooling of the incubator 5. Heating may be performed by providing a heater inside the storage chamber 21 rather than by circulating gas through the first gas circulation circuit 7.

=Conveying Chamber=

The conveying chamber 27 is provided in the interior of the conveyor body 2 and is separated from the exterior of the conveyor body 2. The conveying chamber 27 connects the storage chambers 21 to 26 with the connection opening 281 being the first opening. The conveying chamber 27 is equipped with the conveyor device 9, the mounting table 283 and the sealing member 282.

The mounting table 283 is provided below (−Z) the connection opening 281 and has the incubator 5 mounted thereon in a manner opposing the connection opening 281. The structure of the mounting table 283 is the same as the mounting table 214. Here, a guide plate for preventing the position of the incubator 5 mounted on the mounting table 283 to shift along the Y axis direction may be provided on both sides along the Y axis direction of the mounting table 283.

The connection opening 281 is in communication with the connection opening 181 of the chamber 10 via the coupling unit 101. Here the connection opening 181 is provided to the side plate 18 in a manner such that the working chamber 17 (FIG. 2) and the conveying chamber 27 are connected in a state maintained airtight from the exterior. The path of the connection opening 181 may be of a length same as the path D12 of the connection opening 281. The connection opening 181 may be opened/closed with the door 182 provided to the chamber 10. The door 182 is opened/closed by a worker outside the working chamber 17 and using the gloves 121, 122 and 123. The working chamber 17 is maintained in a state airtight from the exterior when the door 182 is closed. In other words, the working chamber 17 and the conveying chamber 27 in this case are in a state separated from each other. On the other hand, the working chamber 17 and the conveying chamber 27 are in communication when the door 182 is opened.

Further, each incubator 5 has an opening 53A as the second opening for bringing in and taking out the body to be cultured with the isolator 1. The connection opening 281 is configured to be smaller than the outer circumference of the incubator 5 but larger than the opening 53A. In other words, the path D12 of the connection opening 281 is set to be shorter than the path (outer circumference of the incubator 5) of the front plate 53 of the incubator 5 but longer than the path D11 of the opening 53A.

The sealing member 282 is, for example, a rubber gasket which allows the culture chamber 53B (FIG. 9) and the working chamber 17 to communicate in a manner maintained airtight from the exterior of the culture chamber 53B and the working chamber 17 when the incubator 5 is pushed thereagainst. The sealing member 282 is fixed to the surrounding of the connection opening 281 of the back plate 201 using such as adhesives. The path of the sealing member 282 is set longer than the path D11 of the opening 53A but shorter than the path of the outer circumference of the front plate 53 such that the sealing member 282 comes against the surrounding of the opening 53A (FIG. 6) at the front plate 53 of the incubator 5 when the incubator 5 is pushed thereagainst.

Further the conveying chamber 27 has provided an inlet hole (not shown) for gas to flow into the conveying chamber 27 and an outlet hole (not shown) for gas in the conveying chamber 27 to flow out, and the first gas circulation circuit 7C allows the gas to flow in and out. Description of the first gas circulation circuit 7C will be given later.

=Conveyor Device=

<Configuration of the Conveyor Device>

The conveyor device 9 is a device that conveys to mount on the mounting table 283 the incubators 5 stored in the storage chambers 21 to 26 and convey the incubators 5 mounted on the mounting table 283 to the storage chambers 21 to 26. Further, the conveyor device 9 may also push against the gasket 282 the incubator 5 mounted on the mounting table 283.

The conveyor device 9 includes a first rail 91, a second rail 94, a first moving body 92, a second moving body 97 (FIG. 5), conveying tables 95, 96 and a column member 93.

The first rail 91 is provided along the horizontal direction (Y axis). The first rail 91 is provided between the storage chambers 21 to 26 and the mounting table 283, in the X direction.

The first moving body 92 moves along the first rail 91. The first moving body 92 includes a first motor 92A which is controlled by the controller 3 to move in the +Y direction or the −Y direction based on the drive force transmitted from the first motor 92A.

The column member 93 is fixed on the first moving body 92 such that the longitudinal direction of the column member 93 comes along the vertical direction (Z axis). Therefore, the column member 93 moves along the Y axis direction along with the movement of the first moving body 92 along the Y axis direction.

The second rail 94 is provided to the column member 93 so to come along the vertical direction.

The second moving body 97 moves along the second rail 94. The second moving body 97 includes a second motor 97A which is controlled by the controller 3 to move upward (+Z) or downward (−Z) based on the drive force transmitted from the second motor 97A.

The conveying table 95 is fixed to the second moving body 97. The conveying table 95 is in a substantially rectangular form when seen from the +Z direction toward the −Z direction. The conveying table 95 is set such that the width in the X axis direction is longer than the width in the Y axis direction. The conveying table 95 moves along the Z axis direction along with the movement of the second moving body 97 along the Z axis direction.

The conveying table 96 has a shape similar to that of the conveying table 95. The conveying table 96 is provided on the conveying table 95 in a manner movable along the X axis direction with respect to the conveying table 95. For example, a rail extending in the X axis direction may be provided on the top face (+Z) of the conveying table 95 to allow the conveying table 96 move along this rail. Further, the conveying table 96 is assumed to move on the conveying table 95 toward the +X direction or the −X direction based on the drive force transmitted from the third motor 95A controlled by the control device 3. Here, the conveying table 95 may be made to move along the X axis direction by transforming the rotational force of the motor into the force which acts in the X axis direction using a rack and pinion mechanism.

The conveying table 96 may be moved by controlling the first motor 92A, the second motor 97A and the third motor 95A with the control device 3 depending on the X, the Y and the Z axis directions. And the conveying table 96 exhibits a function as an arm that conveys the incubator 5 inside the conveyor body 2 and that transmits force acting toward the +X side with respect to the incubator 5 mounted on the mounting table 283.

<Operation of the Conveyor Device>

When the incubator 5 stored in the storage chamber 21 is conveyed on the mounting table 283, the conveying table 96 opposes the storage chamber 21 and the first motor 92A and the second motor 97A are controlled such that the conveying table 96 moves to a position in the Z axis direction that comes between the mounting table 214 and the bottom plate 96, as well. Thereafter, the third motor 95A is controlled such that the conveying table 96 is moved to the storage chamber 21 side (−X). By controlling in this way, the conveying table 96 moves in the Z axis direction through the notch part 214A to be arranged below the incubator 5. The second motor 97A is controlled so that the conveying table 96 moves upward. By controlling in this way, the incubator 5 is mounted on the conveying table 96 to allow conveying of the incubator 5. Thereafter, the conveying table 96 is appropriately moved so that the incubator 5 is mounted on the mounting table 283.

The incubators 5 stored in the storage chambers 21 to 26 are also mounted on the mounting table 283 by moving the conveying table 96 in a manner similar to that of the incubator 5 stored in the storage chamber 21.

The conveying table 96 is moved to a position that opposes the back plate 51 of the incubator 5 mounted on the mounting table 283. The third motor 95A is controlled so that the conveying table 96 is moved to the +X side. In this situation, the back plate 51 is applied a force acting in the direction from the −X side to the +X side with the conveying table 96. The front plate 53 of the incubator 5 is pushed against the sealing member 282 based on this force applied by the conveying table 96. At this time, the opening 53A is made to be positioned inside the connection opening 281 when seen from the isolator 1 side (+X) toward the −X side.

Further, the incubator 5 mounted on the mounting table 283 is conveyed to the storage chambers 21 to 26 by appropriately moving the conveying table 96.

===Depository Body===

Figure 7:
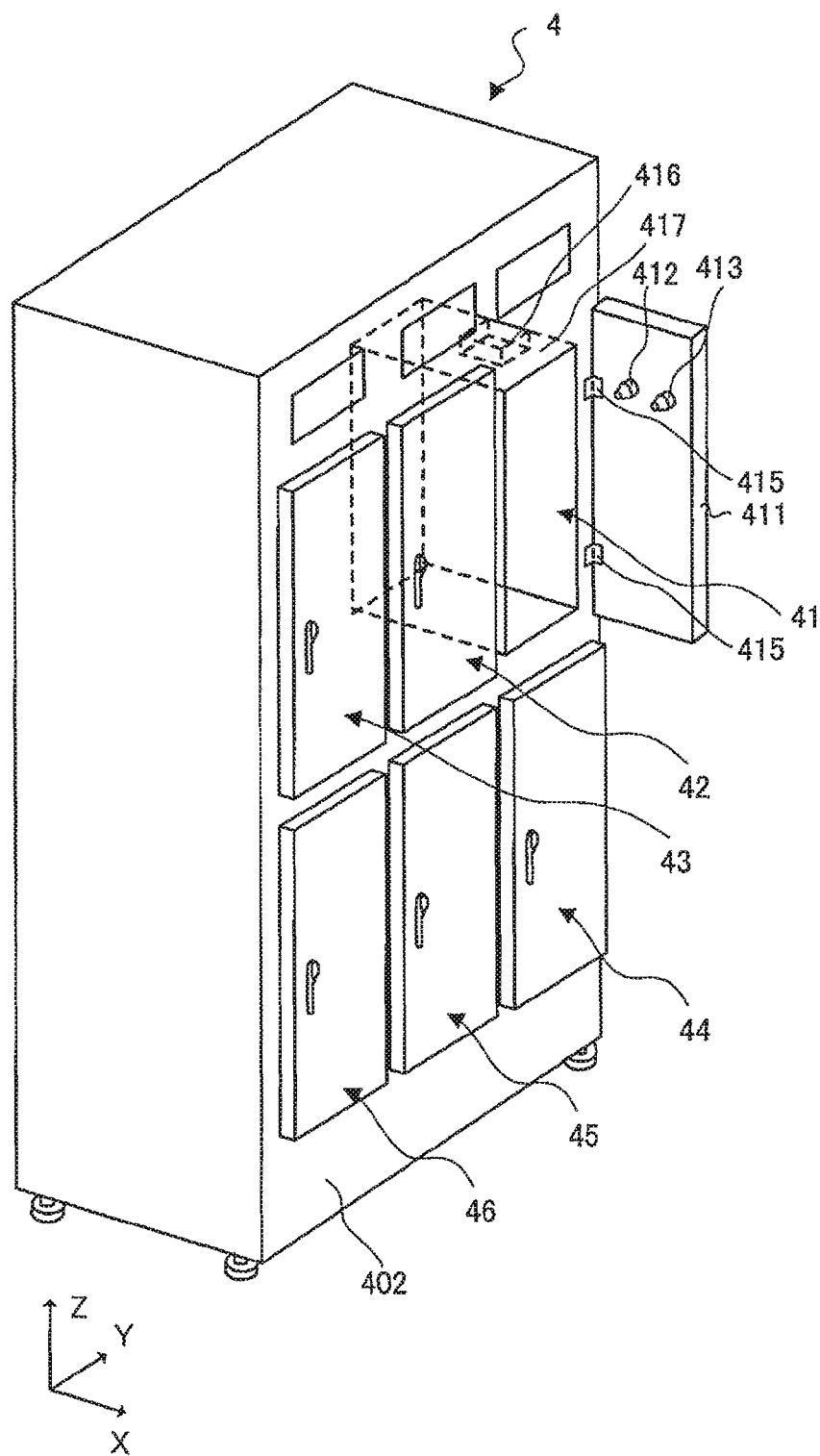
FIG. 7 is a perspective view illustrating a depository body according to the first embodiment of the present invention.

Description of the depository body according to the present embodiment will be given in the following with reference to FIGS. 1 and 7. FIG. 7 is a perspective view illustrating a depository body according to the present embodiment. Although the interior of the depository chamber 41 and the reading device 416 are in hidden states, they are indicated in dashed lines for the purpose of illustration.

The depository body 4 is a device that stores and has deposited the incubator 5 in the depository chambers 41 to 46. The depository body 4 is provided in the periphery of the conveyor body 2 so that a worker can easily move the incubator 5 between the depository body 4 and the conveyor body 2. The front plate 402 of the depository body 4 may be made to face the +X side.

The depository body 4 is a metal box in a substantially rectangular parallelepiped form. And the contour of the depository body 4 including the front plate 402 may be formed by, for example, bending and welding or attaching predetermined metal plates so to restrain bacterial invasion from the exterior to the interior of the depository body 4 and also to keep the interior of the depository body 4 airtight.

The depository body 4 includes the depository chambers 41 to 46, a second gas circulation circuit 6B and a first gas circulation circuit 7B. In other words, the depository body 4 partitions at least the depository chambers 41 to 46.

==Depository Chamber==

The depository chambers 41 to 46 are provided to have three depository chambers arranged along the horizontal direction (Y axis) and in pairs along the vertical direction (Z direction). Here, the number of depository chambers provided to the depository body 4 may be less than six or more than six. And the depository chambers need not be arranged side by side along the vertical direction and the horizontal direction.

The interiors of the depository chambers 41 to 46 are separated from each other. The structures of the depository chambers 41 to 46 are the same with each other so that description of only the depository chamber 41 will be given and description of the structures of the depository chambers 41 to 46 will be omitted.

The depository chamber 41 has the shape of the interior thereof in a substantially rectangular parallelepiped form. The inner shape of the depository chamber 41 is formed larger than the contour of the incubator 5 so that the incubator 5 can be stored in the depository chamber 41. The interior of the depository chamber 41 may be chamfered to allow easy cleaning.

The depository chamber 41 is opened/closed using the door 411 in a substantially rectangular parallelepiped form. The door 411 is provided on the +X side of the depository chamber 41 and separates the interior of the depository chamber 41 from the exterior thereof. The door 411 is provided to rotate about a rotating shaft extending along the Z axis running through the hinge 415. Here, a sealing member such as a rubber gasket may be provided to the edge of the door 411 to keep the interior of the depository chamber 41 airtight when the door 411 is closed.

The inner face of the door 411 facing the interior of the depository chamber 41 is equipped with a supply port 412 and a discharge port 413. The supply port 412 is used to supply gas to the interior of the incubator 5 which is stored in the depository chamber 41 and the discharge port 413 is used to discharge gas discharged from the incubator 5. In other words gas flows out through the supply port 412 and gas flows in through the discharge port 413. The supply port 412 and the discharge port 413 are respectively provided at positions opposing the supply port 552 and the discharge port 553 of the incubator 5.

The second locking device equipped to the depository body 4 is locked when the door 411 is closed. In this way the door 411 cannot be opened. The second locking device is controlled by the control device 3 and performs the locking and the releasing of the door 411. When the second locking device releases the lock, the door 411 is openable.

When the door 411 is closed in a state having the incubator stored in the depository chamber 41, the supply port 412 and the discharge port 413 are respectively connected to the supply port 552 and the discharge port 553 of the incubator 5. On the other hand, when the door 411 is opened, the supply port 412 and the discharge port 413 are released from the supply port 552 and the discharge port 553 of the incubator 5. The supply and the discharge of gas through the supply port 412 and the discharge port 413 are performed by the second gas circulation circuit 6B (FIG. 10). The details of the second gas circulation circuit 6B will be given later.

The depository chamber 41 has a reading device 416 provided in the interior thereof. The reading device 416 is provided to the top plate 417 and has a configuration similar to that of the reading device 215.

Further, the depository chamber 41 has provided an inlet hole (not shown) for gas to flow into the depository chamber 41 and an outlet hole (not shown) for gas to flow out of the depository chamber 41 and the first gas circulation circuit 7B allows the gas to flow in and out. Description of the first gas circulation circuit 7B will be given later.

===Incubator===

Figure 8:
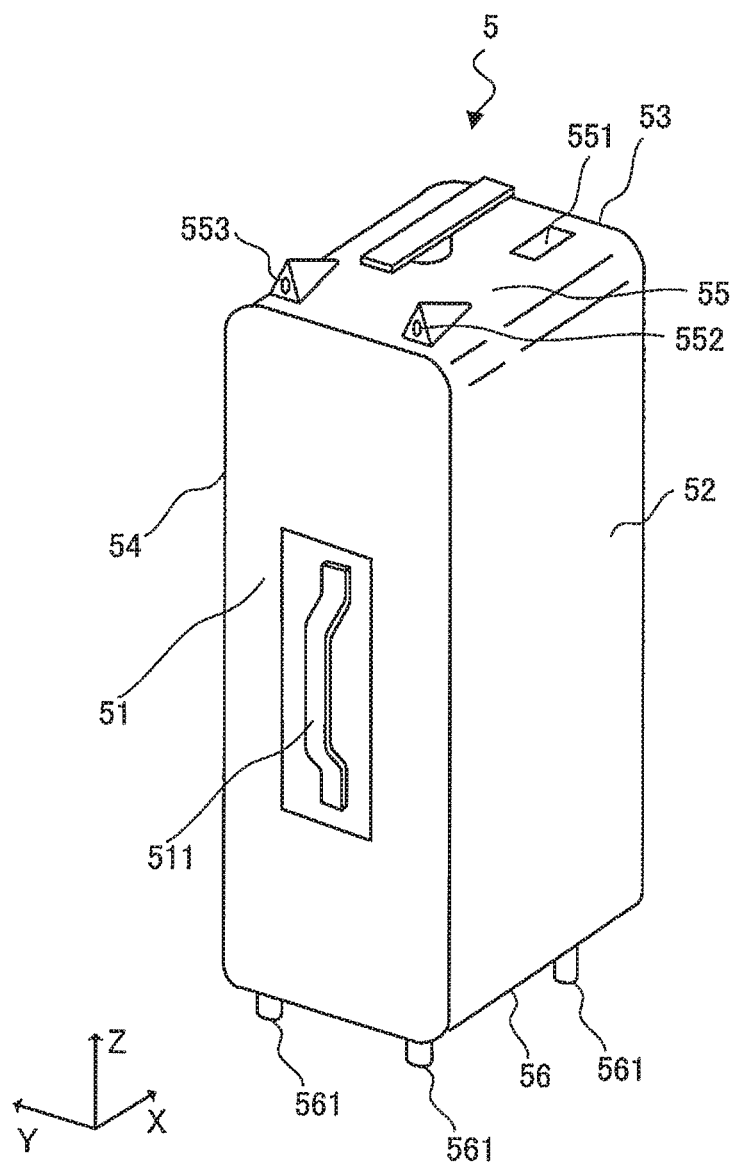
FIG. 8 is a perspective view illustrating the incubator according to the first embodiment of the present invention.
Figure 9:
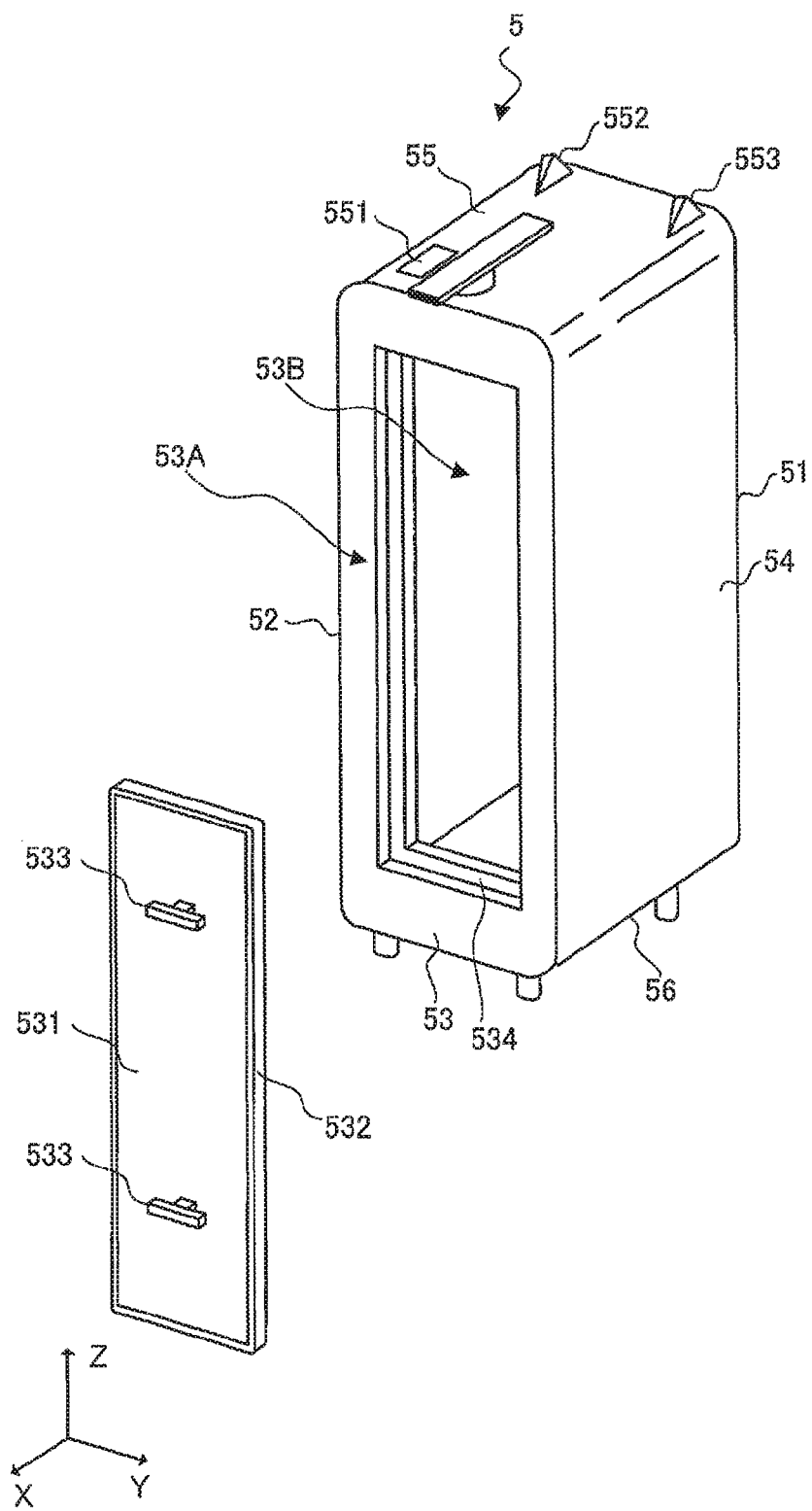
FIG. 9 is a perspective view illustrating the incubator in a state having a lid taken off according to the first embodiment of the present invention.

Description of the incubator according to the present embodiment will be given with reference to FIGS. 8 and 9. FIG. 8 is a perspective view illustrating the incubator according to the present embodiment. FIG. 9 is a perspective view illustrating the incubator in a state having the lid taken off according to the present embodiment.

The incubator 5 is a metal box having a hollow structure so to partition an incubator chamber 53B for storing the body to be cured inside. The contour of the incubator 5 is in a substantially rectangular parallelepiped form. The incubator 5 is detachably stored in the storage chambers 21 to 26 and the depository chambers 41 to 46.

The incubator 5 has the interior separated from the exterior thereof by the back plate 51, the side plates 52, 54, the front plate 53, the bottom plate 56 and the top plate 55 (also called the "shell members of the incubator 5".) Here, the shell members of the incubator 5 may be formed by, for example, bending and welding or attaching predetermined metal plates so to restrain bacterial invasion from the exterior to the interior of the incubator 5 and also to keep the interior of the incubator 5 airtight.

The incubator 5 includes a handle 511, a tag 551, a supply port 552, a discharge port 553, legs 561, and a lid 531. Further, the incubator 5 need not be metal and can be made with a resin chassis, and here the structure was assumed to be hollow, however, the structure may have insulating material intervening therebetween. Further, a heater may be provided for heating the side walls of the interior for preventing condensation at the interior of the incubator 5.

The lid 531 is in a substantially rectangular shape when seen along the direction from the +X side toward the −X side. The lid 531 is provided to the front plate 53 and is used to open/close the opening 53A to communicate with the incubator chamber 53B. The outer path of the lid 531 is set shorter than the path of the opening 53A such that the lid 531 fits to the opening 53A. A sealing member 532 is provided to the outer circumference of the lid 531. The sealing member 532 is, for example, a rubber gasket which is provided to keep the incubator chamber 53B airtight when the opening 53A is closed with the lid 531.

The lid 531 is provided with a knob 533 which exhibits a function as a handle for handling the lid 531 when opening/closing the opening 53A. A worker can open/close the opening 53A by holding the knob 533 and moving the lid 531.

When closing the opening 53A, the lid 531 is kept in a state parallel to the front plate 53 and moved to the opening 53A side (−X side). The lid 531 comes into contact with the stepped part 534 in the opening 53A for the opening 53A to be closed with the lid 531. In this case, the sealing member 532 is sandwiched and deformed between the lid 531 and the periphery of the opening 53A. And the elastic force applied by the sealing member 532 to the lid 531 allows the lid 531 to be fixed with the self-weight thereof to a degree such that the lid 531 does not come off from the opening 53A. Here in this case, the incubator chamber 53B is maintained in a state airtight from the exterior.

When the opening 53A is to be opened, a force directed in the direction from the −X side to the +X side is applied to the knob 533. The lid 531 separates from the opening 53A based in this force applied.

The incubator 5 was explained to be realizable with a resin chassis instead of a metal chassis, however, the incubator 5 may have the interior thereof made visible by forming with transparent resin or providing a transparent window to the lid 531. Here, the heater for heating may adopt a transparent electrode such as an indium tin oxide (ITO) to secure a visible interior.

The tag 551 stores therein information (also referred as "identification information") for identifying the incubator 5. The tag 551 is an IC tag that performs near field communication based on Radio Frequency Identification (RFID) between the reading device inside the storage chamber among the storage chamber 21 to 26 in which the incubators 5 are stored and the reading device inside the depository chamber among the depository chambers 41 to 46 in which the incubators 5 are stored. Here, the tag 551 may be made to perform wireless communication based on methods besides RFID between the reading devices. Additionally, the tag 551 may be a tag having attached a code such as a bar code or the code itself which has information read with the aforementioned reading device. Here in this case, the code is assumed to be a code for identifying an incubator 5.

The supply port 552 and the discharge port 553 are gas supply and discharge openings which are used when performing supply and discharge of gas to and from the incubator chamber 53B. The supply port 552 and the discharge port 553 are provided on the back plate 51 side (−X) end on the top plate 55 and are in communication with the incubator chamber 53B. The supply port 552 and the discharge port 553 are faced toward the −X side. For such reason, when, for example, the door 211 is closed in a state having the incubator 5 stored in the storage chamber 21, the supply port 552 and the discharge port 553 are respectively connected to the supply port 212 and the discharge port 213. And when, for example, the door 411 is closed in a state having the incubator 5 stored in the depository chamber 41, the supply port 552 and the discharge port 553 are respectively connected to the supply port 412 and the discharge port 413.

When the incubators 5 are stored in the storage chambers 21 to 26, the back plate 51 is stored facing the front plate 202 side (−X). And when the incubators 5 are stored in the depository chambers 41 to 46, the back plate 51 is stored facing the front plate 402 side (+X).

The handle 511 is provided to the back plate 51 and is used, for example, when the incubator 5 stored in the storage chamber 21 and the depository chamber 41 is taken out from side of the doors 211 and 411.

A plurality of legs 561 are provided to the bottom plate 56.

===Gas Circulation Circuit===

Description of the gas circulation circuits according to the present embodiment will be given in the following with reference to FIGS. 10 and 11. FIG. 10 is a view illustrating a second gas circulation circuit according to the present embodiment. FIG. 11 is a view illustrating a first gas circulation circuit according to the present embodiment.

=Second Gas Circulation Circuit=

The second gas circulation circuit 6 is a circuit used when performing supply and discharge of gas to and from the incubators 5 stored in the storage chambers 21 to 26. Here, the second gas circulation circuit 6 may be provided to each of the storage chambers 21 to 26 so that the incubators 5 which are stored in each storage chamber have the supply and discharge of gas performing separately. Additionally, the second gas circulation circuit 6 may be provided to each predetermined combination of the storage chambers 21 to 26 so that the incubators 5 stored in each storage chamber combination have the supply and discharge of gas performing separately. Further, only a single second gas circulation circuit 6 may be provided so that the incubators 5 stored in each storage chamber have the supply and discharge of gas performed in an integrated manner.

The second gas circulation circuit 6B is a circuit used when performing supply and discharge of gas to and from the incubators stored in the depository chambers 41 to 46. The second gas circulation circuit 6B, similar to the second gas circulation circuit 6, may be provided to each depository chamber, may be provided to each combination of the depository chambers or may have only one provided to the depository chambers. Since the structure of the second gas circulation circuits 6 and 6B are similar, description of only the second gas circulation circuit 6 will be given and description of the second gas circulation circuit 6B will be omitted.

The second gas circulation circuit 6 includes a sterilizing gas generation unit 661, an environmental equipment 662, solenoid valves V1, V2, a first pump P1, a second pump P2, a first filter 664 and a second filter 663.

The sterilizing gas generation unit 661 is a device which exhibits a function as a sterilization device for supplying sterilizing substances. The sterilizing gas generation unit 661 is a device which generates sterilizing gas by aerifying or gasifying sterilizing substances, for example, a hydrogen peroxide solution and the like. The environmental equipment 662 is a device that adjusts the humidity, the temperature, the carbon dioxide concentration and the like of the air supplied to the environmental equipment 662. The solenoid valves V1, V2 are, for example, three-way valves for changing the flow path of the gas. The first pump P1 generates positive pressure to supply gas from the solenoid valve V1 through the supply ports 212, 552 and to the incubator chamber 53B. The second pump P2 generates negative pressure to supply gas from the incubator chamber 53B through the discharge ports 553, 213 and to the solenoid valve V2. The first filter 664 is, for example, a High Efficiency Particulate Air (HEPA) filter for removing impurities such as dust included in the gas supplied to the incubator 5. The second filter 663 is a device for reducing the concentration and detoxifying the sterilizing gas included in the gas discharged from the incubator 5. The second filter 663 is assumed to include a catalyst such as platinum, activated carbon and the like for decomposing sterilizing substances.

The solenoid valve V1, the first pump P1, the incubator 5, the second pump P2, the solenoid valve V2 and the environmental equipment 662 are annularly connected with the piping 61. The sterilizing gas generation unit 661 is connected between the solenoid valve V2 and the environmental equipment 662 so that the generated sterilizing gas flows into the piping 61. The solenoid valve V1 has one end of the piping 62 connected thereto for allowing external air to flow in through the first filter 664. The solenoid valve V2 has one end of the piping 63 connected thereto for allowing gas in the second gas circulation circuit 6 to be discharged through the second filter 663. In other words, the second filter 663 is provided to the discharge path through which gas in the incubator chamber 53B is discharged.

=First Gas Circulation Circuit=

The first gas circulation circuit 7 is a circuit used to perform supply and discharge of gas to and from the storage chambers 21 to 26. The first gas circulation circuit 7, similar to the second gas circulation circuit 6, may be provided to each storage chamber, may be provided to each combination of the storage chambers or may have only one provided to the storage chambers.

The first gas circulation circuit 7B is a circuit used to perform supply and discharge of gas to and from the depository chambers 41 to 46. The first gas circulation circuit 7B, similar to the first gas circulation circuit 7, may be provided to each depository chamber, may be provided to each combination of the depository chambers or may have only one provided to the depository chambers.

The first gas circulation circuits 7A, 7C are respectively circuits used to perform supply and discharge of gas to and from the working chamber 17 and the conveying chamber 27. Since the structure of the first gas circulation circuits 7, 7A, 7B and 7C are similar, description of only the first gas circulation circuit 7C will be given and description of the first gas circulation circuits 7, 7A and 7B will be omitted.

The first gas circulation circuit 7C includes a sterilizing gas generation unit 761, an environmental equipment 762, solenoid valves V3, V4, a first pump P3, a second pump P4, a first filter 764 and a second filter 763. The configurations of the sterilizing gas generation unit 761, the environmental equipment 762, the solenoid valves V3, V4, the first pump P3, the second pump P4, the first filter 764 and the second filter 763 are respectively the same as the configurations of the sterilizing gas generation unit 661, the environmental equipment 662, the solenoid valves V1, V2, the first pump P1, the second pump P2, the first filter 664 and the second filter 663.

===Control Device===

Figure 12:
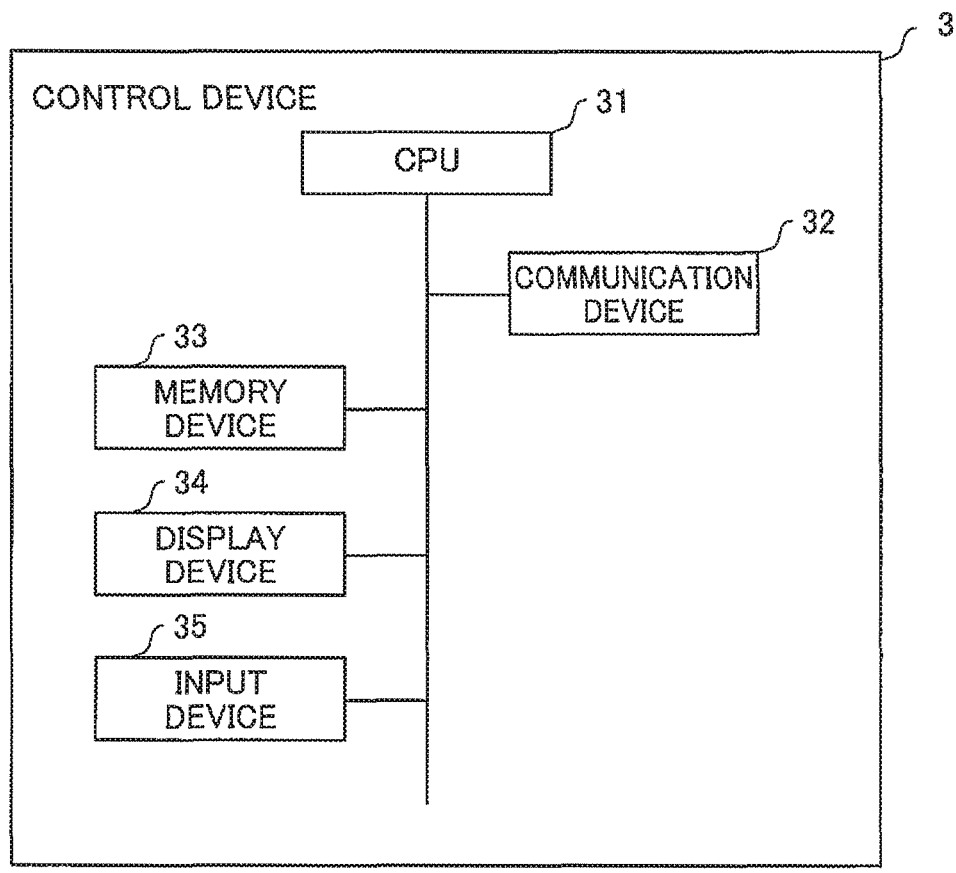
FIG. 12 is a block diagram illustrating hardware of a control device according to the first embodiment of the present invention.
Figure 13:
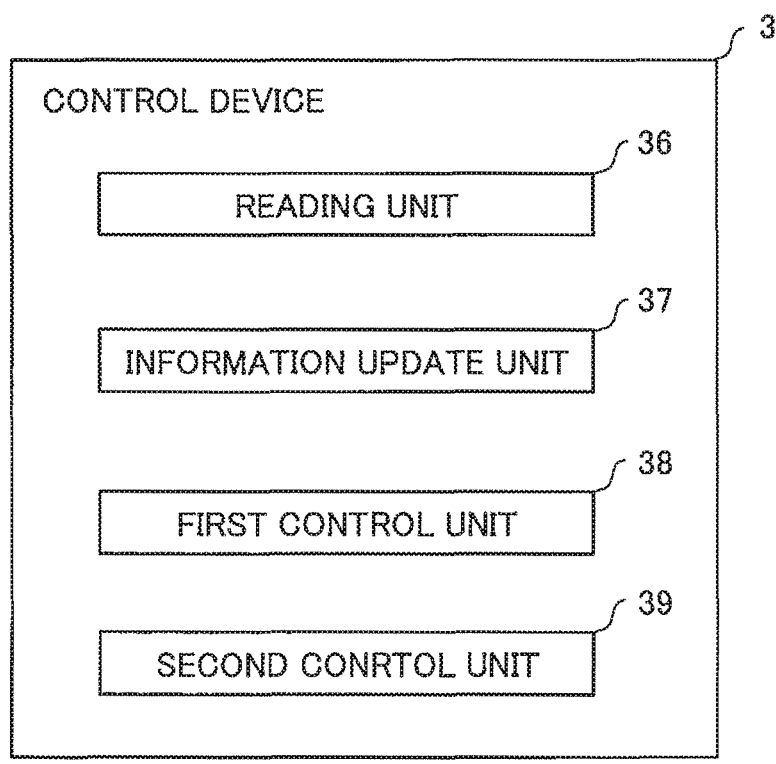
FIG. 13 is a block diagram illustrating the control device according to the first embodiment of the present invention.

Description of the control device according to the present embodiment will be given in the following with reference to FIGS. 12 through 14. FIG. 12 is a block diagram illustrating the hardware of a control device according to the present embodiment. FIG. 13 is a block diagram illustrating the control device according to the present embodiment. FIG. 14 is a diagram illustrating incubator information according to the present embodiment.

The control device 3 includes a Central Processing Unit (CPU) 31, a communication device 32, a memory device 33, a display device 34 and an input device 35. The CPU 31 implements various functions of the control device 3 by executing programs stored in the memory device 33 and performs overall control of the control device 3. The memory device 33 has the aforementioned programs and various information stored therein. The display device 34 is a display that displays information of the control device 3. The input device 35 is, for example, a keyboard, a mouse and the like for inputting information to the control device 3. The communication device 32 performs communication between the control devices 100, 200 and 400 via the communication line N1.

The control device 3 further includes a reading unit 36, an information update unit 37, a first control unit 38 and a second control unit 39 (also referred as the "various functions of the control device 3".) The various functions of the control device 3 are implemented by executing the CPU 31 of the programs stored in the memory device 33.

The reading unit 36 reads the information stored in the tag 551 of the incubator 5 stored in each storage chamber by communicating between the reading devices provided to the storage chambers 21 to 26.

The information update unit 37 updates the incubator information T1 based on the information read by the reading unit 36. The incubator information T1 has each of the storage chambers associated with the identification information of the incubators stored in each of the storage chambers and has each of the depository chambers associated with the identification information of the incubators 5 stored in each of the depository chambers. Here, the identification information may include, for example, information indicating the patient corresponding to the body to be cured stored in the incubator 5, information indicating the body itself to be cured, and the like. The incubator information T1 indicates that the storage chambers 22, 23 and 24 respectively have stored therein the incubators 5 which have attached identification information A, B and C and that the depository chambers 41, 43, 45 and 46 respectively have stored therein the incubators 5 which have attached identification information D, E, F and G. The incubator information T1 further indicates that the incubator 5 is not stored in the storage chambers 21, 25 and 26 and the depository chambers 42 and 44.

The first control unit 38 controls the environment of the isolator system 110. Description of the first control unit 38 will be given later.

The second control unit 39 controls the operation of the isolator system 110. Specifically, the second control unit 39 controls the first and the second locking devices based on information input by the worker through the input device 35 (FIG. 12.) Here, the worker inputs information indicating the storage chamber or the depository chamber whose lock is to be released. For example, the display device 34 may be displaying the incubator information T1 for a worker to input the information based on the displayed incubator information T1. For example, when the worker inputs information which indicates the storage chamber 21 and the depository chamber 41, the second control unit 39 controls to release the locks of the door 211 and the door 411.

Further, the second control unit 39 controls, based on the information input by the worker through the input device 35, the conveying of the incubators 5 stored in each of the storage chambers to the connection opening 281 side and the conveying of the incubators 5 from the connection opening 281 side to each storage chamber.

===First Control Unit===

Description of the first control unit of the present embodiment will be given in the following with reference to FIGS. 10 and 11.

The first control unit 38 controls the second gas circulation circuits 6 and 6B and the first gas circulation circuits 7, 7A, 7B and 7C (also referred as the "gas circulation circuits") to control the environments of each of the incubator chambers 53B of the incubators 5 stored in the storage chambers, the incubator chambers 53B of the incubators 5 stored in the storage chambers, the depository chambers, the working chamber 17 and the conveying chamber 27 (also referred as the "chambers".) Here, controlling the environment means adjusting the chamber temperature, the humidity and the carbon dioxide concentration of the chambers and decontaminating the chambers.

The first control unit 38 and the second gas circulation circuits 6, 6B exhibit the functions as the environment control device which individually controls the interior environment of the plurality of incubators 5 by performing supply and discharge of gas to and from the plurality of incubators 5.

The configurations of the first control unit 38 controlling the gas circulation circuits are the same so that description of only the first control unit 38 controlling the second gas circulation circuit 6 will be given and description of the configurations of the first control unit 38 controlling the second gas circulation circuit 6B and the first gas circulation circuits 7, 7A, 7B and 7C will be omitted.

=Decontamination of Incubator=

The first control unit 38 controls the solenoid valves V1, V2, the first pump P1 and the second pump P2 so that gas circulates in the order of the first solenoid valve V1, the first pump P1, the incubator chamber 53B, the second pump P2 the solenoid valve V2 and the environmental equipment 662 through the piping 61. Further, the first control unit 38 generates sterilizing gas from the sterilizing gas generation unit 661. In this situation, the sterilizing gas circulates the annular circuit including the incubator chamber 53B to sterilize the incubator chamber 53B.

Thereafter, the first control unit 38 stops the sterilizing gas generation unit 661 and then controls the solenoid valves V1, V2, the first pump P1 and the second pump P2 so that the external air is discharged through the first filter 664, the piping 62, the solenoid valve V1, the first pump P1, the incubator chamber 53B, the second pump P2, the solenoid valve V2, the piping 63 and the second filter 663. In this case, the sterilizing gas filled in the incubator chamber 53B is discharged.

=Adjusting Temperature, Humidity and Carbon Dioxide Concentration in the Incubator=

As mentioned above, the first control unit 38 controls to circulate gas. Further, the first control unit 38 controls the environmental equipment 662 to adjust the temperature, the humidity, the carbon dioxide concentration and the like of the gas flowing through the environmental equipment 662. The gas that has been adjusted by the environmental equipment 662 is supplied to the incubator chamber 53B so that the temperature, the humidity and the carbon dioxide concentration in the incubator chamber 53B is adjusted.

=Modes=

The first control unit 38 is assumed to include a mode that controls the environment of any one of the chambers and a mode that simultaneously controls a plurality of the environments selected from the chambers. In other words, for example, the first control unit 38 includes such as a mode to control only the environment of the working chamber 17, a mode to control only the environment of the conveying chamber 27, a mode to control the environments of both the working chamber 17 and the conveying chamber 27.

===Operation of Isolator System===

Figure 15:
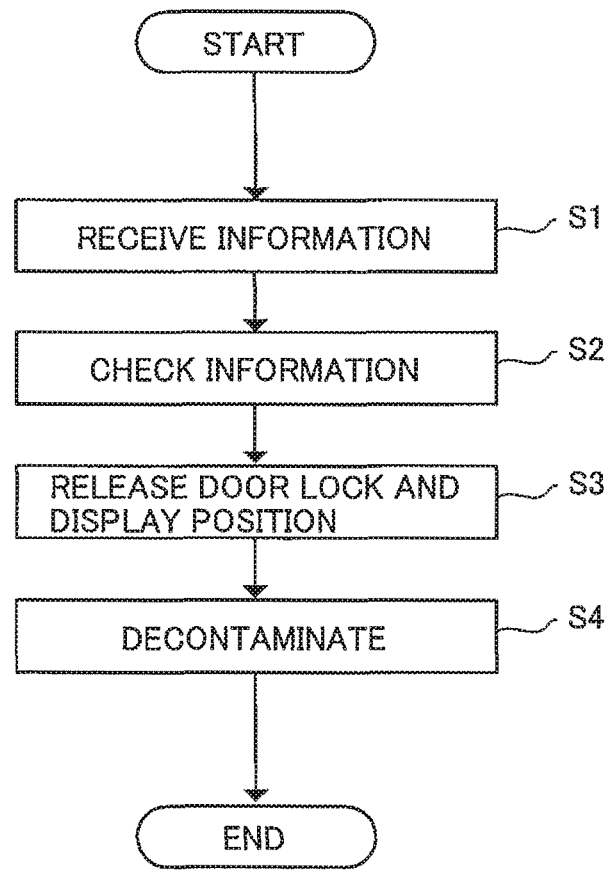
FIG. 15 is a flow chart illustrating operations performed when the incubator is taken out from the depository chamber according to the first embodiment of the present invention.
Figure 16:
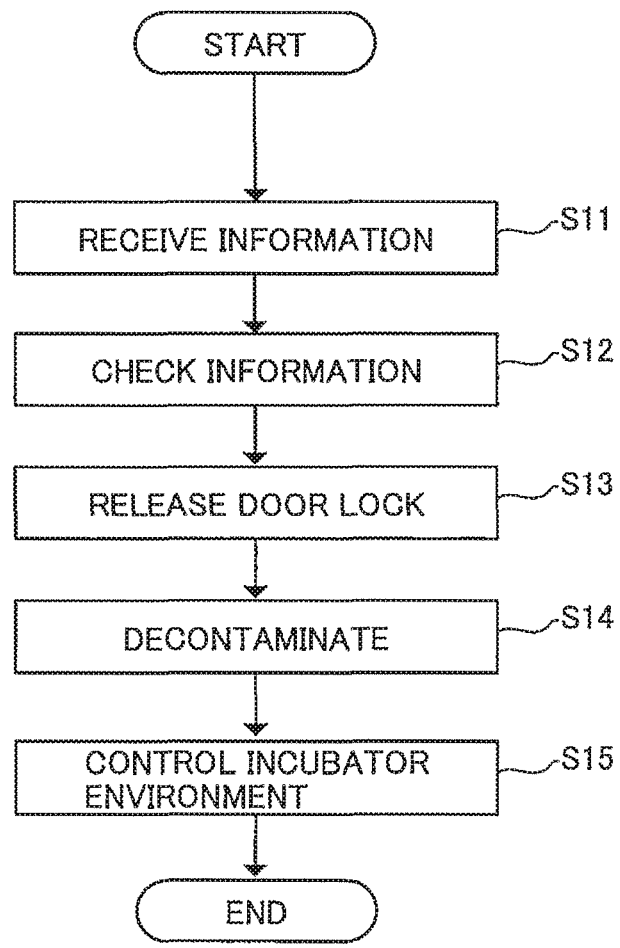
FIG. 16 is a flow chart illustrating operations performed when the incubator is stored in the storage chamber according to the first embodiment of the present invention.
Figure 17:
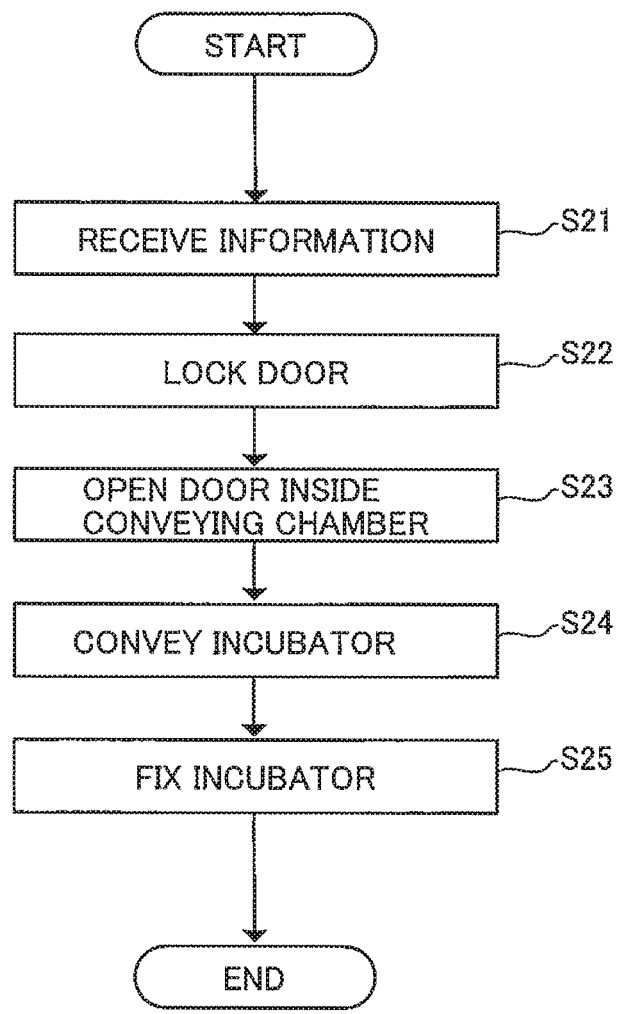
FIG. 17 is a flow chart illustrating operations performed when the incubator is conveyed from the storage chamber to the connection opening side according to the first embodiment of the present invention.
Figure 18:
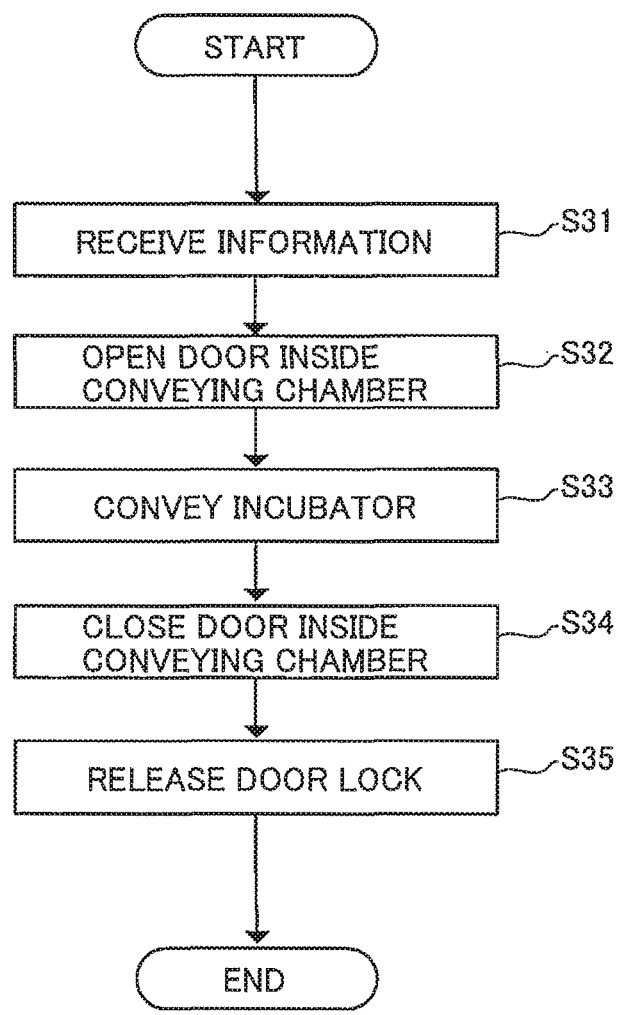
FIG. 18 is a flow chart illustrating operations performed when the incubator is conveyed from the connection opening side to the storage chamber according to the first embodiment of the present invention.

Description of the isolator system according to the present embodiment will be given in the following with reference to FIGS. 4 to 7 and FIGS. 15 to 18. FIG. 15 is a flow chart illustrating operations performed when the incubator is taken out from the depository chamber according to the present embodiment. FIG. 16 is a flow chart illustrating operations performed when the incubator is stored in the storage chamber according to the present embodiment. FIG. 17 is a flow chart illustrating operations performed when the incubator is conveyed from the storage chamber to the connection opening side according to the present embodiment. FIG. 18 is a flow chart illustrating operations performed when the incubator is conveyed from the connection opening side to the storage chamber according to the present embodiment.

<Operations Performed when Incubator 5 is Taken Out from Depository Chamber 41>

A worker inputs identification information D. The control device 3, after receiving the identification information D (Step S1), checks the identification information D in the incubator information T1 (Step S2). The control device 3 releases the lock of the door 411 of the depository chamber 41 corresponding to the identification information D and displays on the display device 34 information indicating the depository chamber 41 (Step S3).

A worker, based on the display of the display device 34, opens the door 411 to take out the incubator 5 from the depository chamber 41 and thereafter closes the door 411. The control device 3 after locking the door 411 performs decontamination of the depository chamber 41 (Step S4). Hereafter, the control device 3 updates the incubator information T1 based on information read by the reading devices.

The operations performed when taking the incubators 5 out from the depository chambers 42 to 46 are the same as the operation performed when taking the incubator 5 out from the depository chamber 41. Additionally, the operations performed when taking the incubators 5 out from the storage chambers 21 to 26 are also the same as the operation performed when taking the incubator 5 out from the depository chamber 41.

<Operations Performed when Storing Incubator 5 in Storage Chamber 21>

A worker inputs information indicating the storage chamber 21. The control device 3, after receiving information indicating the storage chamber 21 (Step S11), checks the information indicating the storage chamber 21 in the incubator information T1 (Step S12). For example, the control device 3 may determine whether the incubator 5 is stored in the storage chamber 21 and when an incubator 5 is already stored, the control device 3 displays an alarm on the display device 34. After the operation of Step S12, the control device 3 releases the lock of the door 211 of the storage chamber 21 and displays on the display device 34 information indicating that the lock has been released (Step S13).

The worker, based on the display of the display device 34, opens the door 211 to store the incubator 5 in the storage chamber 21 and thereafter closes the door 211. The control device 3 after locking the door 211 performs decontamination of the storage chamber 21 (Step S14). The control device 3 updates the incubator information T1 based on the information read by the reading devices. Hereafter, the control device 3 controls the environment of the incubator chamber 53B of the incubator 5 (Step S15).

The operations performed when the incubators 5 are stored in the storage chambers 22 to 26 are the same as the operation performed when storing the incubator 5 in the storage chamber 21. Additionally, the operations performed when the incubators 5 are stored in the depository chambers 41 to 46 are the same as the operation performed when the incubator 5 is stored in the storage chamber 21.

<Operations Performed when Conveying Incubator 5 from Storage Chamber 22 to Connection Opening 281>

A worker inputs identification information A. The control device 3 after receiving identification information A (Step S21) locks the door 221 (FIG. 3) (Step S22). The control device 3 opens the door 226 (FIG. 4) (Step S23). The control device 3 controls the first motor 92A, the second motor 97A and the third motor 95A (referred as the "motors") so that the incubator 5 stored in the storage chamber 22 is conveyed from the storage chamber 22 onto the mounting table 283 (Step S24). The control device 3 controls the motors so that the front plate 53 of the incubator 5 is pushed against the sealing member 282 (Step S25). Hereafter, the second control unit 39 closes the door 226.

When the incubator 5 is pushed against the sealing member 282, the worker outside the working chamber 17 can use the gloves 121 to 123 (FIG. 1) to open the lid 531 of the incubator 5 and move the body to be cured stored inside the incubator chamber 53B to the interior of the working chamber 17. In other words, the body to be cured stored in the incubator chamber 53B can be conveyed into and out from the isolator 1.

The operations performed for conveying the incubators 5 from the storage chambers 21 and 23 to 26 to the connection opening 281 side is the same as the operation performed for conveying the incubator 5 from the storage chamber 22 to the connection opening 281 side.

<Operation Performed when Conveying Incubator 5 from Connection Opening 281 Side to Storage Chamber 22>

A worker inputs information indicating the storage chamber 22. The control device 3, after receiving information indicating the storage chamber 22 (Step S31), opens the door 226 (FIG. 4) (Step S32). The control device 3 controls the motors so that the incubator 5 mounted on the mounting table 283 is conveyed to the storage chamber 22 (Step S33). After closing the door 226 (Step S34), the control device 3 releases the lock of the door 221 (Step S35).

The operations performed when the incubator 5 is conveyed from the connection opening 281 side to the storage chambers 21 and 23 to 26 are the same as the operation performed when the incubator 5 is conveyed from the connection opening side 281 to the storage chamber 22.

Further, the control device 3 is assumed to appropriately control the environments of the chambers.

Second Embodiment

The isolator system according to the second embodiment has the incubator 5 of the isolator system 110 according to the first embodiment changed to an incubator 5B.

===Incubator===

Figure 19:
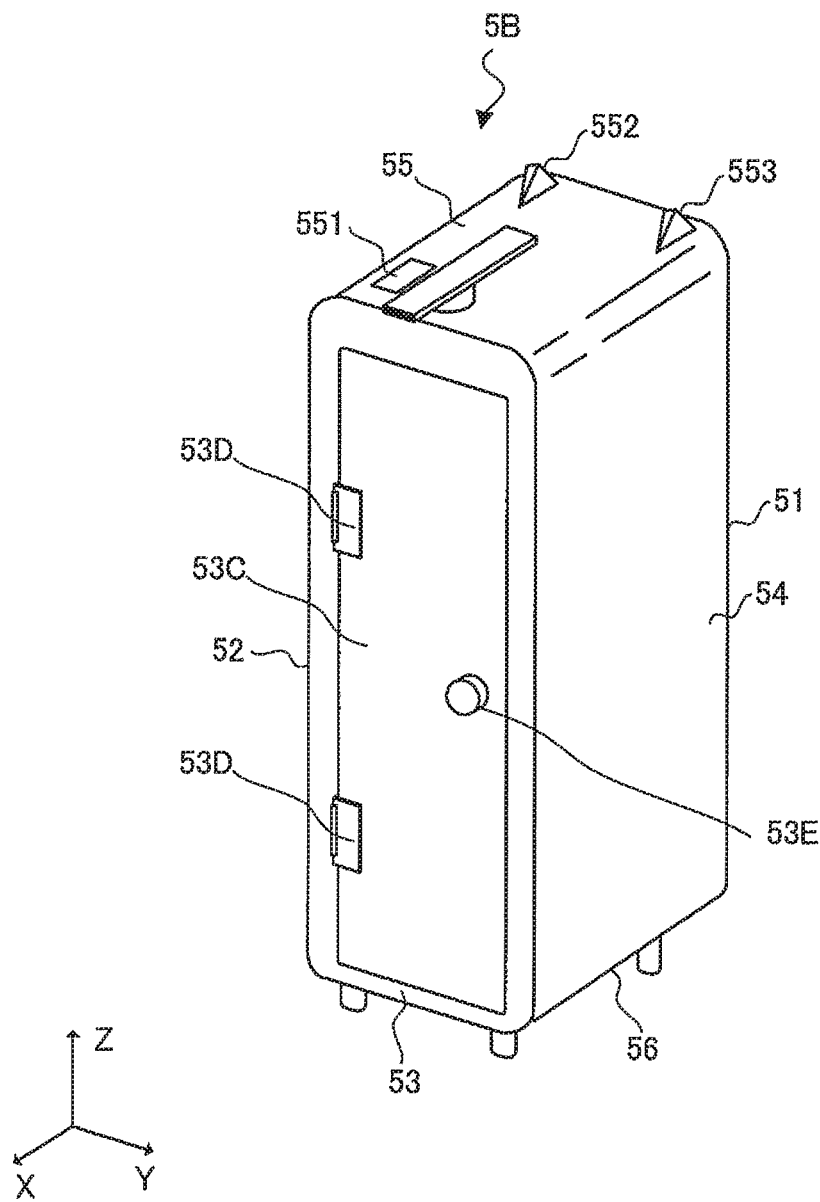
FIG. 19 is a perspective view illustrating an incubator according to a second embodiment of the present invention.

Description of the incubator according to the present embodiment will be given in the following with reference to FIG. 19. FIG. 19 is a perspective view illustrating an incubator according to the present embodiment. Configurations same as that shown in FIG. 9 are attached the same reference numbers and description thereof will be omitted.

The incubator 5B includes a door 53C. The door 53C is a door for opening/closing the opening of the front plate 53. The door 53C is provided to rotate about a rotating shaft extending along the Z axis and running through the hinge 53D. Here, it is assumed that a sealing member such as a rubber gasket is provided to the edge of the door 53C to keep the interior of the incubator 5B airtight when the door 53B is closed.

Additionally, the door 53C is provided with a knob 53E. When the door 53C is closed, a stopper (not shown) of the door 53C catches onto a rest (not shown) provided to the front plate 53 to allow the door 53C to be in an unopenable state. In this case, when the knob 53C is turned, the stopper is released from the rest so that the door 53C comes to be in an openable state.

Third Embodiment

The isolator system according to the third embodiment has the incubator 5 and the conveyor body 2 of the isolator system 110 according to the first embodiment changed to the incubator 8 and the conveyor body 2B, respectively.

===Conveyor Body and Incubator===

Figure 20:
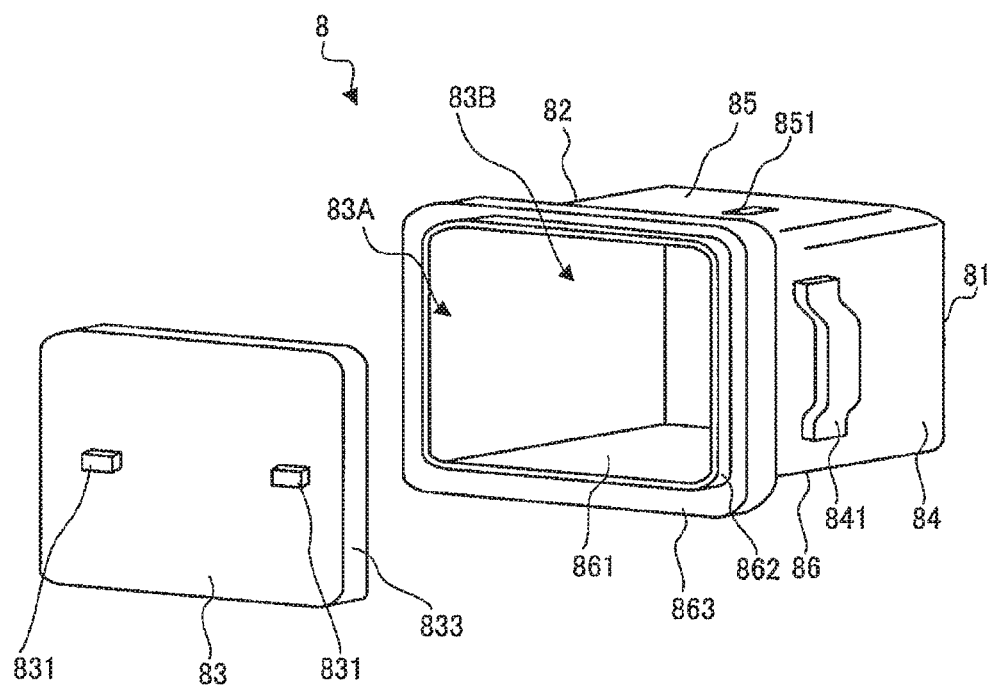
FIG. 20 is a perspective view illustrating an incubator having a lid taken off according to a third embodiment of the present invention.
Figure 21:
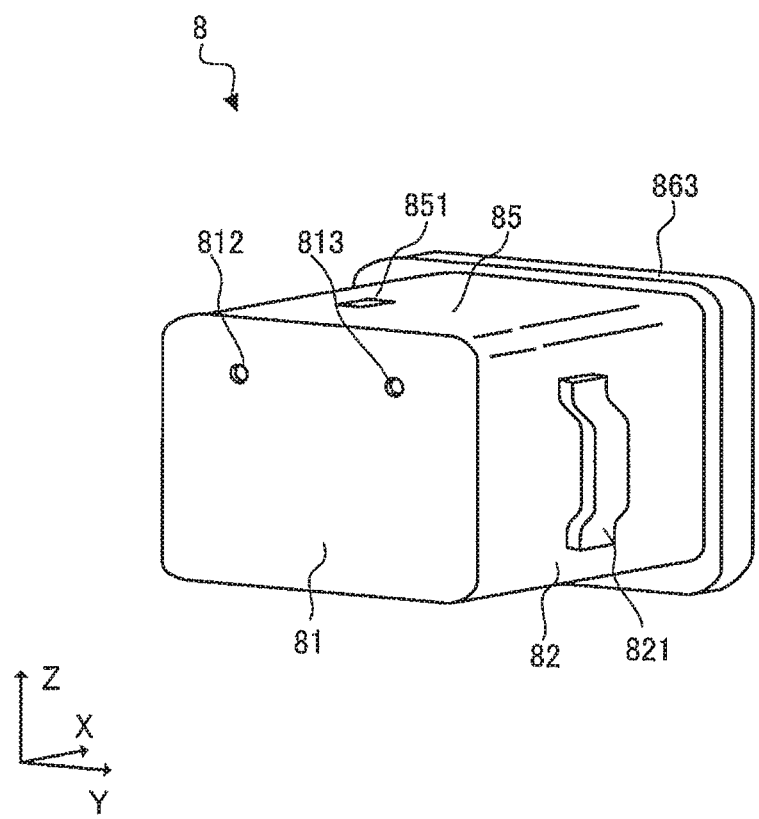
FIG. 21 is a perspective view illustrating the incubator according to the third embodiment of the present invention.
Figure 22:
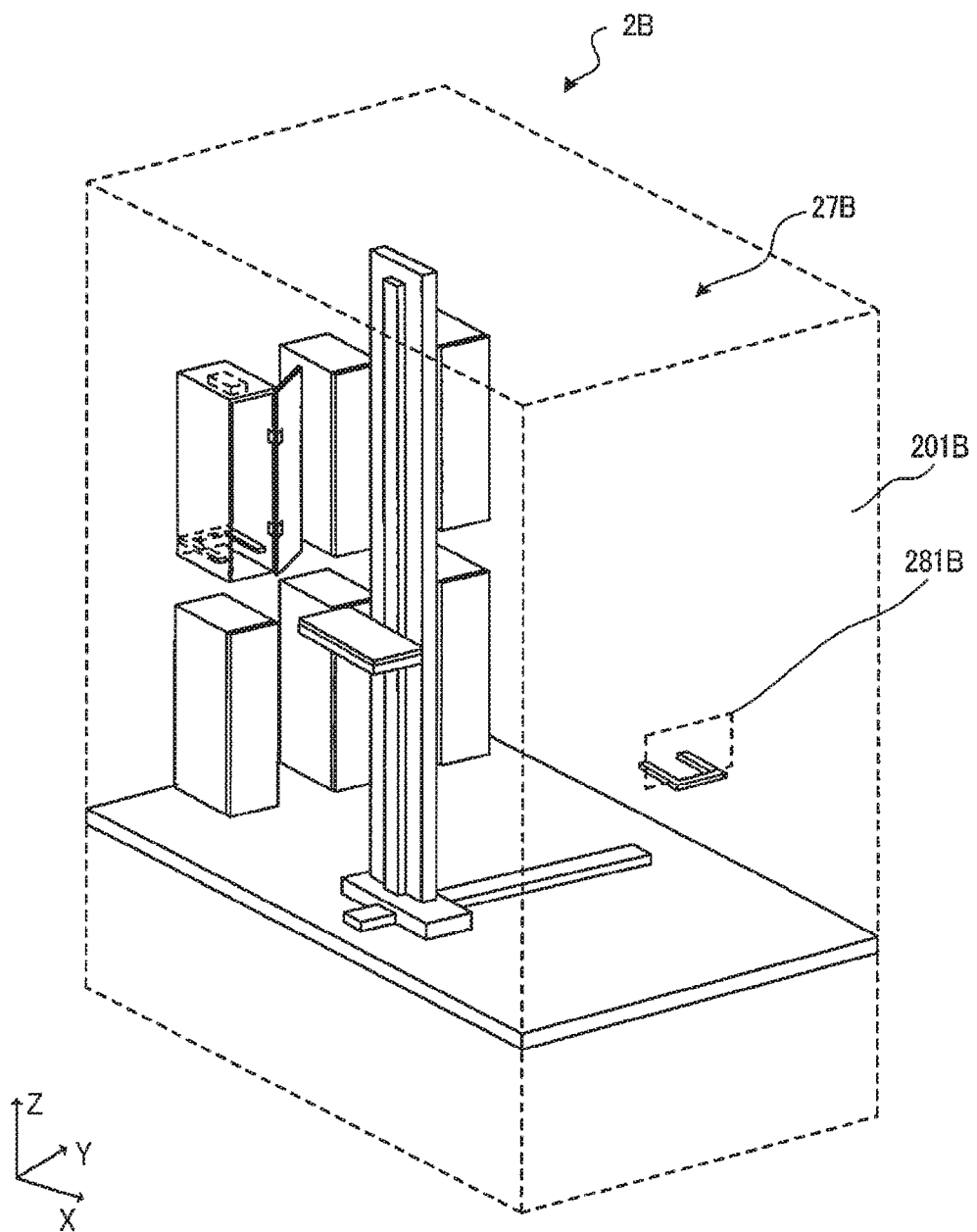
FIG. 22 is a transparent view illustrating a conveyor body according to the third embodiment of the present invention.

Description of the conveyor body and the incubator according to the present embodiment will be given in the following with reference to FIGS. 20 to 22. FIG. 20 is a perspective view illustrating an incubator having the lid taken off according to the present embodiment. FIG. 21 is a perspective view illustrating the incubator according to the present embodiment. FIG. 22 is a transparent view illustrating a conveyor body according to the present embodiment.

The conveyor body 2B has the connection opening 281 of the conveyor body 2 (first embodiment) changed to the connection opening 281B and the sealing member 282 of the conveyor body 2 omitted.

The incubator 8 is a cassette type incubator for curing bodies to be cured. The incubator 8 is a hollow structured metal box allowing the bodies to be cured to be stored in the interior of the incubator chamber 83B. The contour of the incubator 8 is in a substantially rectangular parallelepiped form.

The incubator chamber 83B is structured so that the length of the incubator chamber 83B along the X axis direction and the length of the incubator chamber 83B along the Y axis direction are longer than the length of the incubator chamber 83B along the Z axis direction. Therefore, a plurality of the dishes, flasks and the like which contain the body to be cured can be placed on the bottom 861 of the incubator chamber 83B by making the area of the bottom 861 of the incubator chamber 83B relatively wide.

The incubator 8 has the interior and the exterior thereof separated by the back plate 81, the side plates 82, 84, the bottom plate 86 and the top plate 85. Here, the incubator 8 may have the same structure as the incubator 5 (first embodiment).

The incubator 8 includes handles 841, 821, a tag 851, a supply port 812, a discharge port 813, a lid 83 and a sealing member 863.

The lid 83 is used to open/close the opening 83A which comes into communication with the incubator chamber 83B. The lid 83 is in a substantially rectangular shape when seen along the direction from the +X side toward the −X side. The edges 833 of the lid 83 are bent toward the −X side so to fit to the edges 862 on the +X side of the side plates 82, 84, bottom plate 86 and the top plate 85 from the outside of the incubator 8. The path of the edges 833 of the lid 83 is set to be longer than the path of the edges 862 so that the lid 83 fits to the edges 862. The edges 862 are assumed to have a sealing member (not shown) and the like, for example, a rubber gasket provided so to keep the incubator chamber 83B airtight when the opening 83A is closed with the lid 83.

The lid 83 is provided with a knob 831 which exhibits a function as a handle for handling the lid 83 when opening/closing the opening 83A. A worker can open/close the opening 83A by holding this knob 831 and moving the lid 83.

The sealing member 863 is, for example, a rubber gasket for maintaining the working chamber 17 and the incubator chamber 83B which is in communication with the incubator chamber 83B airtight when the edges 862 side of the incubator 8 are inserted into the connection opening 281B from interior of the conveying chamber 27, and the sealing member 863 comes into contact with the periphery of the connection opening 281B at the back plate 201B. The sealing member 863 is provided along the outer face of the incubator 8. Specifically the sealing member 863 is provided continuously to the side plates 82, 84, bottom plate 86 and the top plate 85. The sealing member 863 is fixed using adhesives and the like. The external path of the sealing member 863 is set to be longer than the path of the connection opening 281B so that the sealing member 863 comes into contact with the periphery of the connection opening 281B at the back plate 201B.

The configurations of the tag 851, the supply port 812 and the discharge port 813 are the same as the configurations of the tag 551 (first embodiment), the supply port 512 and the discharge port 513, respectively.

SUMMARY

As mentioned above, the isolator system 110 or the incubator conveying system includes a conveyor body 2, the plurality of incubators 5, the conveyor device 9, the first control unit 38 and the second gas circulation circuit 6. The isolator system 110 or the incubator conveying system has partitioned the conveyor body 2, the plurality of storage chambers 21 to 26, a connection opening 281 as a first opening connected airtight to such as the isolator 1 as an external equipment and a conveying chamber 27 which connects the plurality of storage chambers 21 to 26 and the connection opening 281. The plurality of incubators 5 are detachably stored in the plurality of the storage chambers 21 to 26. The conveyor device 9 conveys one of the plurality of the incubators 5 stored in the storage chambers 21 to 26 from the storage chamber to the connection opening 281 side. The environment control device including the first control unit 38 and the second gas circulation circuit 6 controls each interior environment of the plurality of the incubators 5 by supplying and discharging gas to and from the respective incubators 5 stored in the storage chambers 21 to 26. Therefore, the incubators 5 can be conveyed from the storage chambers 21 to 26 to the side of the connection opening 281 where the isolator 1 is connected. In other words, the bodies to be cured can be conveyed in units of the incubators 5. Additionally, an isolator system 110 or an incubator conveying system which can control the environment of each respective incubator chamber 53B and is easy to use can be provided.

Further, the isolator system 110 or the incubator conveying system includes a first gas circulation circuit 7C. The first gas circulation circuit 7C includes a sterilizing gas generation unit 761 as a sterilization device that supplies sterilized gas into the conveying chamber 27. Therefore, intrusion of bacteria from the conveying chamber 27 into the incubator chamber 53B and the working chamber 17 can be prevented by sterilizing the conveying chamber 27. Therefore, the incubator chamber 53B and the working chamber 17 can be certainly brought close to a sterile state.

Furthermore, the first gas circulation circuit 7C includes solenoid valves V3, V4, a first pump P3 and a second pump P4 (also referred as the "first circulation device".) The first circulation device exhibits a function as an air conditioning device which discharges gas inside the conveying chamber 27 out of the conveying chamber 27. The first gas circulation circuit 7C further includes a second filter 763. The second filter 763 is provided to the discharge path through which gas discharged out of the conveying chamber 27 passes and includes a catalyst that decomposes the sterilizing substance. Therefore discharge of the sterilizing substances from the isolator system 110 or the incubator conveying system can be prevented. Thus a cracker for decomposing the discharged sterilizing substances is not required so that there can be provided an isolator system 110 or an incubator conveying system which is easy to use and can be placed in any place such as a laboratory of a clinic and the like without the need to select the place to be set.

Yet further still, the isolator system 110 or the incubator conveying system includes a first gas circulation circuit 7. The first gas circulation circuit 7 includes a sterilizing gas generation unit 761 as a sterilization device that supplies sterilizing gas into each of the storage chambers 21 to 26. Therefore, intrusion of bacteria from the storage chambers into the incubator chamber 53B and intrusion of bacteria from the storage chambers, through the conveying chamber 27 and into the working chamber 17 can be prevented by sterilizing the storage chambers. Thus, the incubator chamber 53B and the working chamber 17 can be certainly brought close to a sterile state.

Even further still, the first gas circulation circuit 7 includes a second circulation device which has the same configuration as the first circulation device of the first gas circulation circuit 7C. The second circulation device exhibits a function as an air conditioning device which discharges gas inside the storage chambers 21 to 26 to the outside of the storage chambers 21 to 26. The first gas circulation circuit 7 further includes a second filter which has the same configuration as the second filter 763 of the first gas circulation circuit 7C. This second filter is provided to the discharge path through which gas discharged out of the storage chambers 21 to 26 passes and includes a catalyst that decomposes the sterilizing substances. Therefore discharge of the sterilizing substances from the isolator system 110 or the incubator conveying system can be prevented.

Even further still, the isolator system 110 or the incubator conveying system includes a second gas circulation circuit 6. The second gas circulation circuit 6 includes a sterilizing gas generation unit 661 as a sterilization device that supplies sterilizing gas into each of the incubators 5. Therefore, the incubator chamber 53B can be certainly brought close to a sterile state.

Even further still, the second gas circulation circuit 6 includes solenoid valves V1, V2, a first pump P1 and a second pump P2 (also referred as the "third circulation device".) The third circulation device exhibits a function as an air conditioning device which discharges gas inside the incubator 5 out of the incubator 5. The second gas circulation circuit 6 further includes a second filter 663. The second filter 663 is provided to the discharge path through which gas discharged out of the incubator 5 passes and includes a catalyst that decomposes the sterilizing substances. Therefore the discharge of the sterilizing substances from the isolator system 110 or the incubator conveying system can be prevented.

Even further still, the isolator system 110 or the incubator conveying system includes a depository body 4 which has sectioned a plurality of depository chambers 41 to 46 which can have deposited a plurality of incubators 5. Therefore, for example, the incubators 5 which need not be conveyed by the conveyor body 2 can be deposited in the depository body 4. Therefore, an isolator system 110 or an incubator conveying system which is easy to use can be provided.

Even further still, the controller 3 of the isolator system 110 or the incubator conveying system includes a first control unit 38. The first control unit 38 includes a mode (first mode) which controls only the environment of the working chamber 17, a mode (second mode) which controls only the environment of the conveying chamber 27 and a mode (third mode) which controls both environments of the working chamber 17 and the conveying chamber 27. Therefore the incubator chamber 53B and the working chamber 17 can be certainly brought to a sterile state by executing the modes.

Even further still, the plurality of the incubators 5 are demountable from the outside and the direction (X axis direction) in which the plurality of the incubators 5 are demounted from the outside the conveyor body 2 is a direction same as the direction (X axis direction) in which the plurality of the incubators 5 are demounted by the conveyor device 9. Therefore, the incubators 5 can be conveyed from the storage chambers 21 to 26 to the connection opening 281 side to which the isolator 1 is connected. In other words, the bodies to be cured can be conveyed in units of incubators 5. Further, an isolator system 110 or an incubator conveying system which can control the environment of each respective incubator chamber 53B and is easy to use can be provided. Furthermore, the mounting and demounting of the incubators 5 from the outside and the mounting and demounting of the incubators 5 with the conveyor device 9 can be performed along the X axis direction. Thus, for example, the storing of the incubators 5 into the storage chambers can be certainly and relatively easily performed since, for example, there is no need to move the incubators 5 in the Y axis direction and the Z axis direction in the storage chambers. Further, when the incubators 5 are moved inside the storage chambers, generation of dust by the incubators 5 coming against the storage chambers can be prevented. Furthermore, the isolator system 110 or the incubator conveying system can be provided at relatively low cost since a moving device for moving the incubators 5 along the Y axis direction and the Z axis direction inside the storage chambers is not required.

Even further still, the conveyor device 9 is provided on the opposite side (+X) of the front plate 202 side (−X) of the storage chambers 21 to 26 along the X axis direction. The plurality of the incubators 5 are mounted to the storage chambers 21 to 26 from the outside the conveyor body 2 toward the +X side direction. Further, the plurality of the incubators 5 are mounted to the storage chambers 21 to 26 toward the −X side with the conveyor device 9. In other words the direction (+X) in which the plurality of the incubators 5 are mounted from the outside is in a direction opposite the direction (−X) in which the incubators 5 are mounted with the conveyor device 9. Further, similar to the direction in which the mounting is performed, the direction (−X) in which the plurality of the incubators 5 are removed from the outside is in a direction opposite the direction (+X) in which the plurality of the incubators 5 are removed with the conveyor device 9. Therefore, the incubators 5 are mounted and demounted from both sides of the storage chambers along the X axis direction. Thus, for example, the conveyor device 9 can be prevented from coming in the way to prevent mounting and demounting of the incubators 5 from the outside. In other words, there can be provided an isolator system 110 or an incubator conveying system which is easy to use, such that the incubators 5 can be certainly mounted and demounted to and from the storage chambers from the outside as well as such that the incubators 5 can be certainly mounted and demounted to and from the storage chambers with the conveyor device 9.

Even further still, the storage chambers 21 to 26 respectively include a supply port and a discharge port (first port) for performing supply and discharge of gas to and from the incubators 5. The incubator 5 includes a supply port 552 and a discharge port 553 (second port) which are connected to the supply ports and the discharge ports of the storage chambers 21 to 26. When one of the plurality of the incubators 5 is mounted to, for example, the storage chamber 21 among the plurality of the storage chambers 21 to 26, the supply port 552 and the discharge port 553 are respectively connected to the supply port 212 and the discharge port 213. Therefore, the environments of the incubator chambers 53B can be individually and certainly controlled.

The storage chamber 21 includes a door 211 which opens/closes the storage chamber 21 for mounting and demounting the incubator 5 from the outside. The supply port 212 and the discharge port 213 are provided inside the door 211. The supply port 552 and the discharge port 553 are provided to the door 211 side when the incubator 5 is stored in the storage chamber 21. The supply port 552 and the discharge port 553 are respectively connected to the supply port 212 and the discharge port 213 when the door 211 is closed. Therefore, for example, connection work before closing the door 211 for connecting the supply port 552 and the discharge port 553 to the supply port 212 and the discharge port 213, respectively, is not required. Thus false connection by this connection work can be prevented and the environments of the incubator chambers 53B can be individually and certainly controlled.

The storage chamber 21 includes a door 211 that opens/closes the storage chamber 21 for mounting and demounting the incubator 5 from the outside. The incubator 5 includes a lid 531 which functions as a door which opens/closes the incubator for bringing in and taking out a body to be cured from the isolator 1. The direction (−X) in which the door 211 is opened is opposite the direction (+X) in which the lid 531 of the incubator (FIG. 6) pushed against the sealing member 282 is opened. Therefore, for example, during conveying of the conveyor body 2, the incubator 5 need not be rotated about the rotating shaft extending along the Z axis and running through the incubator 5. Thus, the incubator 5 can be certainly conveyed. Further, since the structure of the conveyor device 9 can be relatively simplified, the number of the components in the conveyor device 9 can be reduced and the conveyor body 2 can be provided at low cost.

Further, each incubator 5 includes an opening 53A as a second opening for bringing in and taking out the body to be cured by the isolator 1. The connection opening 281 is formed smaller than the outer circumference of the incubator 5 but larger than the opening 53A. The incubator 5 is fixed to be pushed against the periphery of the connection opening 281 by the conveyor device 9 and at the same time the opening 53A is arranged to be positioned inside the connection opening 281 when seen from the isolator 1 side. Further, the incubator 5 and the isolator are connected airtight by having provided a sealing member 282 between the incubator 5 and the periphery of the connection opening 281. Therefore, the incubator 5 can be conveyed from the storage chambers 21 to 26 to the side of the connection opening 281 to which the isolator 1 is connected. In other words, the bodies to be cured can be conveyed in units of incubators 5. And an isolator system 110 or an incubator conveying system which is easy to use and can control the environment of each separate incubator chamber 53B can be provided. Further, the working chamber 17 and the incubator chamber 53B can be certainly maintained airtight from the exterior. Therefore, intrusion of bacteria can be prohibited to certainly bring the incubator chamber 53B and the working chamber 17 close to sterile states.

Furthermore, each of the incubators has a tag 551. The tag 551 has stored therein identification information. Each of the storage chambers 21 to 26 includes a reading device for reading identification information. Therefore, the incubators 5 can be conveyed from the storage chambers 21 to 26 to the side of the connection opening 281 to which the isolator 1 is connected. In other words, the bodies to be cured can be conveyed in units of incubators 5. Further, an isolator system 110 or an incubator conveying system which is easy to use and can control the environment of each separate incubator chamber 53B can be provided. Further, for example, the isolator system 110 or the incubator conveying system can be controlled based on identification information stored in the tag 551. Therefore, for example, among the incubators 5, the incubators 5 stored in the storage chambers which are not the target of conveying are prevented from being conveyed.

Yet further still, the depository body 4 (incubator depository) has sectioned a plurality of depository chambers 41 to 46. The depository body 4 includes a plurality of incubators 5, a first control unit 38 and a second gas circulation circuit 6B. The plurality of incubators 5 are demountably stored in the plurality of the depository chambers 41 to 46. The first control unit 38 and the second gas circulation circuit 6B control each separate interior environment of the plurality of the incubators 5 by supplying and discharging gas to and from the incubators 5 stored in the depository chambers 41 to 46. Further, the depository chamber 41 includes a door 411 (first door) for opening/closing the depository chamber 41 to mount or demount the incubator 5 from the outside, and a supply port 412 and a discharge port 413 (first ports) provided inside the door 411 to perform supply and discharge of gas to and from the incubator 5. The incubator 5 includes a supply port 552 and a discharge port 553 (second ports). The supply port 552 and the discharge port 553 are provided to the door 411 side of the incubator 5 stored in the depository chamber 41. The supply port 412 and the discharge port 413 are not connected to the supply port 552 and the discharge port 553 when the door 411 is opened, but are connected when the door 411 is closed. Therefore, the interior environment of the incubators 5 stored in the depository chambers can be controlled separately. Further, for example, connection work before closing the door 411 for connecting the supply port 552 and the discharge port 553 to the supply port 412 and the discharge port 413, respectively, is not required. Thus false connection by this connection work can be prevented and the environment of each incubator chamber 53B can be certainly controlled.

Even further still, the isolator system 110 or the incubator conveying system includes a conveyor body 2, a depository body 4, a plurality of incubators 5, a conveyor device 9, a first control unit 38 and second gas circulation circuits 6, 6B. The conveyor body 2 has sectioned a plurality of the storage chambers 21 to 26, the connection opening 281 which is connected to such as the isolator 1 as an external device and a conveying chamber 27 which connects the plurality of the storage chambers 21 to 26 to the connection opening 281. The plurality of the incubators 5 are demountably stored in the plurality of the storage chambers 21 to 26. The conveyor device 9 conveys one of the plurality of the incubators 5 stored in the storage chambers 21 to 26 from the storage chamber to the connection opening 281 side. The depository body 4 forms the plurality of the depository chambers 41 to 46 which demountably stores the plurality of the incubators 5. The depository chamber 41 includes a door 411 (first door) for opening/closing the depository chamber 41 to mount or demount the incubator 5 from the outside, and a supply port 412 and a discharge port 413 (first ports) provided inside the door 411 to perform supply and discharge of gas to and from the incubator 5. The incubator 5 includes a supply port 552 and a discharge port 553 (second ports). The supply port 552 and the discharge port 553 are provided to the door 411 side of the incubator 5 stored in the depository chamber 41. The supply port 412 and the discharge port 413 are not connected to the supply port 552 and the discharge port 553 when the door 411 is opened, but are connected when the door 411 is closed. Further, the depository chamber 21 includes a door 411 (first door) for opening/closing the depository chamber 21 to mount or demount the incubator 5 from the outside, and a supply port 212 and a discharge port 213 (first ports) provided inside the door 211 to perform supply and discharge of gas to and from the incubator 5. The supply port 552 and the discharge port 553 of the incubator 5 are provided to the door 211 side of the incubator 5 stored in the depository chamber 21. The supply port 212 and the discharge port 213 are not connected to the supply port 552 and the discharge port 553 when the door 211 is opened, but are connected when the door 211 is closed. Further, as mentioned above, the depository chamber 41 includes a door 411, a supply port 412 and a discharge port 413. Therefore, the incubator 5 can be conveyed from the storage chambers 21 to 26 to the side of the connection opening 281 to which the isolator 1 is connected. In other words, the bodies to be cured can be conveyed in units of incubators 5. Additionally, an isolator system 110 or an incubator conveying system which can control the environment of each respective incubator chamber 53B and is easy to use can be provided. For example, connection work before closing the door 211 for connecting the supply port 552 and the discharge port 553 to the supply port 212 and the discharge port 213, respectively, is not required. Thus false connection by this connection work can be prevented and the environments of the incubator chambers 53B can be individually and certainly controlled.

The above first to the third embodiments of the present invention are simply for facilitating the understanding of the present invention and are not in any way to be construed as limiting the present invention. The present invention may variously be changed or altered without departing from its spirit and encompass equivalents thereof.

In the first embodiment, the sealing member 282 was described to be fixed to the back plate 201, however, it is not limited to such. For example, the sealing member 282 (FIG. 4) may be fixed to the periphery of the opening 53A of the front plate 53 of the incubator 5.

Further, in the first embodiment, the incubator 5 was described to be conveyed by the conveyor device 9, however, it is not limited to such. For example, a robot hand which freely moves in the X, Y and Z axis directions may be provided to the conveyor body 2 so that the incubator 5 is conveyed with this robot hand.

Furthermore, in the first present embodiment, the isolator 1 was described to be coupled (connected) to the conveyor body 2 through the connection opening 281, however, it is not limited to such. For example, the depository device for having deposited the body to be cured, the curing device for curing the body to be cured, the observation device for observing the body to be cured and the like which are external devices other than the isolator 1, may be coupled (connected) to the conveyor body 2 through the connection opening 281.

What is claimed is:

1. An incubator conveying system comprising:
a conveyor body including a plurality of storage chambers, a first opening connected to an external device, and a conveying chamber that connects the plurality of storage chambers and the first opening;
a plurality of incubators demountably stored in the plurality of storage chambers, respectively;
a conveyor device configured to convey one of the plurality of incubators from a corresponding one of the storage chambers to the first opening; and
an environment control device configured to supply and discharge gas to and from each of the plurality of incubators and control each interior environment of the plurality of incubators,
wherein the environment control device is selectively coupled and decoupled to each of the plurality of incubators.

2. The incubator conveying system according to claim 1 further comprising a sterilization device configured to supply a sterilizing substance into the conveying chamber.

3. The incubator conveying system according to claim 2, further comprising:
an air conditioning device configured to discharge out of the conveying chamber gas inside the conveying chamber; and
a catalyst configured to be provided to a discharge path through which gas discharged out of the conveying chamber passes and to decompose the sterilizing substance.

4. The incubator conveying system according to claim 1 further comprising a sterilization device configured to supply a sterilizing substance into each of the storage chambers.

5. The incubator conveying system according to claim 4, further comprising:
an air conditioning device configured to discharge out of the storage chambers gas in each of the storage chambers; and
a catalyst configured to be provided to a discharge path through which gas discharged out of the storage chamber passes and to decompose the sterilizing substance.

6. The incubator conveying system according to claim 1 further comprising a sterilization device configured to supply a sterilizing substance into each of the incubators.

7. The incubator conveying system according to claim 6, further comprising:
an air conditioning device configured to discharge out of the incubators gas in each of the incubators; and
a catalyst configured to be provided to a discharge path through which gas discharged out of the incubator passes and to decompose the sterilizing substance.

8. The incubator conveying system according to claim 1 further comprising a depository body including a plurality of depository chambers that has deposited therein the plurality of incubators, respectively.

9. The incubator conveying system according to claim 1, wherein the plurality of incubators are demountable from an outside and a direction in which the plurality of incubators are mounted/demounted from the outside is in a direction same as a direction in which the plurality of incubators are mounted/demounted by the conveyor device.

10. The incubator conveying system according to claim 9, wherein
a direction in which the plurality of incubators are mounted from the outside is in a direction opposite a direction in which the plurality of incubators are mounted by the conveyor device and
a direction in which the plurality of incubators are demounted from the outside is in a direction opposite a direction in which the plurality of incubators are demounted by the conveyor device.

11. The incubator conveying system according to claim 9, wherein
each of the storage chambers has a first port to perform supply and discharge to and from the incubators, each of the incubators has a second port that is connected to the first port, and the first port and the second port are connected when one of the plurality of incubators is mounted to one of the plurality of storage chambers.

12. The incubator conveying system according to claim 11, wherein each of the storage chambers has a first door to open/close the storage chamber to mount/demount the incubator from the outside, the first port is provided inside the first door, the second port is provided on a first door side in the incubator, and the first port and the second port are connected by closing the first door.

13. The incubator conveying system according to claim 10, wherein each of the storage chambers has a first door to open/close the storage chamber to mount/demount the incubator from the outside, each of the incubators has a second door to open/close the incubator to bring into and take out from the external device a culture, and a direction in which the first door is opened is opposite a direction in which the second door is opened.

14. The incubator conveying system according to claim 9 further comprising a depository body including a plurality of depository chambers that has deposited therein the plurality of incubators, respectively.

15. The incubator conveying system according to claim 1, wherein each of the incubators has a second opening to bring into and take out from the external device a culture, the first opening is formed to be smaller than an outer circumference of the incubator and larger than the second opening, the incubator is pushed against a periphery of the first opening by the conveyor device to be fixed and is arranged such that the second opening is positioned inside the first opening when seen from an external device side, and the incubator and the external device are connected airtight by providing a sealing member between the incubator and the first opening.

16. The incubator conveying system according to claim 1, wherein each of the incubators has body identification information and each of the storage chambers has a reading unit configured to read the body identification information.

17. The incubator conveying system according to claim 1, wherein each of the plurality of storage chambers includes a door which is movable between an open state and a closed state.

18. The incubator conveying system according to claim 17, wherein the environment control device is selectively coupled and decoupled to each of the plurality of incubators based on whether the corresponding door is in the open state or the closed state.

19. The incubator conveying system according to claim 18, wherein the environment control device is coupled to each of the plurality of incubators when the corresponding door is in the closed state.

20. The incubator conveying system according to claim 18, wherein the environment control device is decoupled from each of the plurality of incubators when the corresponding door is in the open state.

* * * * *